US012690972B2

(12) United States Patent
Josse et al.

(10) Patent No.: US 12,690,972 B2
(45) Date of Patent: Jul. 28, 2026

(54) EXPANDABLE INTER-BODY DEVICE, SYSTEM, AND METHOD

(71) Applicant: Warsaw Orthopedic, Inc., Warsaw, IN (US)

(72) Inventors: Loic Josse, Palm Beach Garden, FL (US); Muriel Cazin, Caluire-et-Cuire (FR)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 19/046,653

(22) Filed: Feb. 6, 2025

(65) Prior Publication Data

US 2025/0262057 A1     Aug. 21, 2025

Related U.S. Application Data

(60) Provisional application No. 63/555,635, filed on Feb. 20, 2024.

(51) Int. Cl.
| | |
|---|---|
| *A61B 17/84* | (2006.01) |
| *A61F 2/30* | (2006.01) |
| *A61F 2/44* | (2006.01) |
| *A61B 17/56* | (2006.01) |

(52) U.S. Cl.
CPC ........ *A61F 2/30749* (2013.01); *A61B 17/846* (2013.01); *A61F 2/4455* (2013.01); *A61B 2017/564* (2013.01); *A61F 2002/30476* (2013.01)

(58) Field of Classification Search
CPC ............ A61F 2002/30841; A61F 2/447; A61F 2/4611; A61F 2/30749; A61B 17/846; A61B 17/725
See application file for complete search history.

(56) References Cited

U.S. PATENT DOCUMENTS

| | | | | |
|---|---|---|---|---|
| 8,343,219 | B2 * | 1/2013 | Allain | ................... A61F 2/4455 606/100 |
| 9,039,774 | B2 * | 5/2015 | Chataigner | ............. A61F 2/447 606/86 A |
| 9,044,337 | B2 * | 6/2015 | Dinville | ................ A61F 2/4455 |
| 9,351,847 | B2 | 5/2016 | Reed et al. | |

(Continued)

OTHER PUBLICATIONS

European Search Report in Application No. 25157431.5 dated Jun. 30, 2025.

*Primary Examiner* — Jacqueline T Johanas

(74) *Attorney, Agent, or Firm* — FOX ROTHSCHILD LLP

(57)     ABSTRACT

A bone pin installation system is disclosed. The bone pin installation system may include a hollow surgical tool extending in a longitudinal direction and may have a guide portion at a distal end thereof. The system may include one or more bone pins having a curved body and a support arm. The system may also include one or more connector plates having a superior surface, an inferior surface and one or more pin seats extending between the superior surface and the inferior surface. The pin seats may be configured to receive at least one of the bone pins so that the support arm is pivotally supported by the superior surface. The guide portion may include one or more channels configured to receive the support arm of the one or more bone pins and guide the corresponding bone pin during an installation procedure.

20 Claims, 21 Drawing Sheets

(56) References Cited

U.S. PATENT DOCUMENTS

| | | | | |
|---|---|---|---|---|
| 10,398,565 B2 * | 9/2019 | Bender | ................ | A61F 2/4455 |
| 11,007,066 B2 | 5/2021 | Kaufmann et al. | | |
| 11,672,674 B2 * | 6/2023 | Shoshtaev | ............ | A61F 2/4455 |
| | | | | 623/17.16 |
| 2011/0230971 A1 * | 9/2011 | Donner | ............... | A61B 17/846 |
| | | | | 606/246 |
| 2013/0245767 A1 * | 9/2013 | Lee | ......................... | A61F 2/442 |
| | | | | 623/17.16 |
| 2014/0156010 A1 | 6/2014 | Lee et al. | | |
| 2017/0135822 A1 * | 5/2017 | Bender | ................ | A61F 2/4611 |
| 2017/0304080 A1 * | 10/2017 | Lee | ......................... | A61F 2/447 |
| 2017/0311997 A1 * | 11/2017 | Lequette | .............. | A61F 2/4611 |
| 2018/0325694 A1 * | 11/2018 | Petersheim | .......... | A61F 2/4455 |
| 2019/0000638 A1 * | 1/2019 | Gilbride | ................ | A61F 2/447 |
| 2023/0225869 A1 * | 7/2023 | Lee | .................... | A61F 2/30749 |
| | | | | 623/23.39 |
| 2023/0285160 A1 | 9/2023 | Shoshtaev et al. | | |
| 2023/0355396 A1 * | 11/2023 | Perryman | ............ | A61B 17/846 |
| 2023/0390078 A1 * | 12/2023 | Bergey | ................ | A61F 2/4455 |
| 2025/0262057 A1 * | 8/2025 | Josse | ................ | A61B 17/1757 |

* cited by examiner

800

601b

610

604

600

608

602a

601a

602b 116
130
105b
105a
104
122
114
102

100

300

300

1500

500

2000

EXPANDABLE INTER-BODY DEVICE, SYSTEM, AND METHOD

CROSS-REFERENCE TO RELATED APPLICATION

This application claims the benefit of and priority to U.S. Provisional Patent Application No. 63/555,635 filed Feb. 20, 2024, the entire disclosure of which is incorporated by reference herein.

FIELD

The present disclosure generally relates to medical devices for the treatment of musculoskeletal disorders, and more particularly to a surgical device that includes a bone pin anchoring system, and systems and tools for implanting and manipulating the bone pin anchoring system in conjunction with an expandable spinal implant, and a method for using the same.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, they may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods and interbody devices can be used to provide stability to a treated region. For example, during surgical treatment, interbody devices may be introduced to a space between adjacent vertebral bodies (the interbody space) to properly space the vertebral bodies and provide a receptacle for bone growth promoting materials, e.g., grafting. Bone fasteners such as screws and pins may be used to anchor these interbody devices in the interbody space.

An existing problem is that bone fasteners must often be positioned by the surgeon at a particular orientation and angle relative to other components of the surgical treatment prior to deployment. The surgeon must also often make a determination on the depth at which to deploy the bone fasteners into the vertebral bodies. These determinations on the part of the surgeon leave room for error and can increase deployment time of the bone fasteners.

In addition, screw type bone fasteners generally cannot have a curved body because it is not possible to drill curved pilot holes to receive the screws. Curved bone pins pose an advantage over screws in that curved bone pins are less prone to backing out of the vertebral bodies than screws. In addition, the footprint required by the surgeon to deploy screws is greater than for impacting pins. Pin impaction is also faster than screw fastening because multiple pins can be impacted at substantially the same time, whereas, it is not practical to fasten multiple screws at once.

A further problem is instability of existing expandable interbody devices as they are inserted and expanded. Often, the load-bearing surfaces move relative to one another, as well as relative to an inserter, as the interbody device is expanded such that there is a risk of undesired shifts in the positioning of the interbody device within the interverterbral space. Additionally, and depending at least partly on the particular insertion technique employed, anatomical features such as the iliac crest and rib cage pose challenges to the adjustment of inter-body designs in situ.

The present disclosure seeks to address these and other shortcomings in the existing relevant arts.

SUMMARY

One aspect of the disclosure relates to an anchoring system for use in a surgical procedure. The system includes one or more bone pins having a curved body extending from a proximal end to a distal end, and the proximal end comprising a support arm. The system also includes a connector plate having a superior surface, an inferior surface, and one or more pin seats extending between the superior surface and the inferior surface, wherein each of the one or more pin seats are configured to receive a corresponding one of the one or more bone pins such that the support arm of the corresponding one or more bone pins is pivotally supported. The curved body of the one or more bone pins is configured to facilitate anchoring of the one or more bone pins in bony anatomy.

Another aspect of the disclosure relates to a bone pin installation system. In one aspect, the system includes a hollow surgical tool extending in a longitudinal direction and having a guide portion at a distal end thereof. The system also includes one or more bone pins having a curved body extending from a proximal end to a distal end and a support arm. The system still further includes one or more connector plates having a superior surface, an inferior surface and one or more pin seats extending between the superior surface and the inferior surface, wherein the one or more pin seats are configured to receive a corresponding one of the one or more bone pins so that the support arm of the corresponding bone pin is pivotally supported by the superior surface. The guide portion includes one or more channels configured to receive the support arm of a corresponding one of the one or more bone pins and guide the corresponding bone pin during an installation procedure. The curved body of the one or more bone pins is configured to facilitate anchoring of the one or more bone pins in bony anatomy.

Another aspect of the disclosure relates to a method of inserting an expandable spinal implant. The method includes preparing a spinal implant for insertion in a patient, removing a degenerative portion of patient anatomy, inserting the spinal implant between one or more bony structures of the patient, preparing one or more anchoring systems, as disclosed herein, for insertion into the patient, wherein each of the one or more bone pins of the anchoring system is pre-loaded into one or more anchor apertures of a guide portion. The method further includes an aligning step including aligning a guide rod of the guide portion with a central aperture of an endplate of the spinal implant and an impacting step including impacting the one or more anchoring systems into bony anatomy using a pusher. The method still further includes locking one or more locking mechanisms of the spinal implant.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
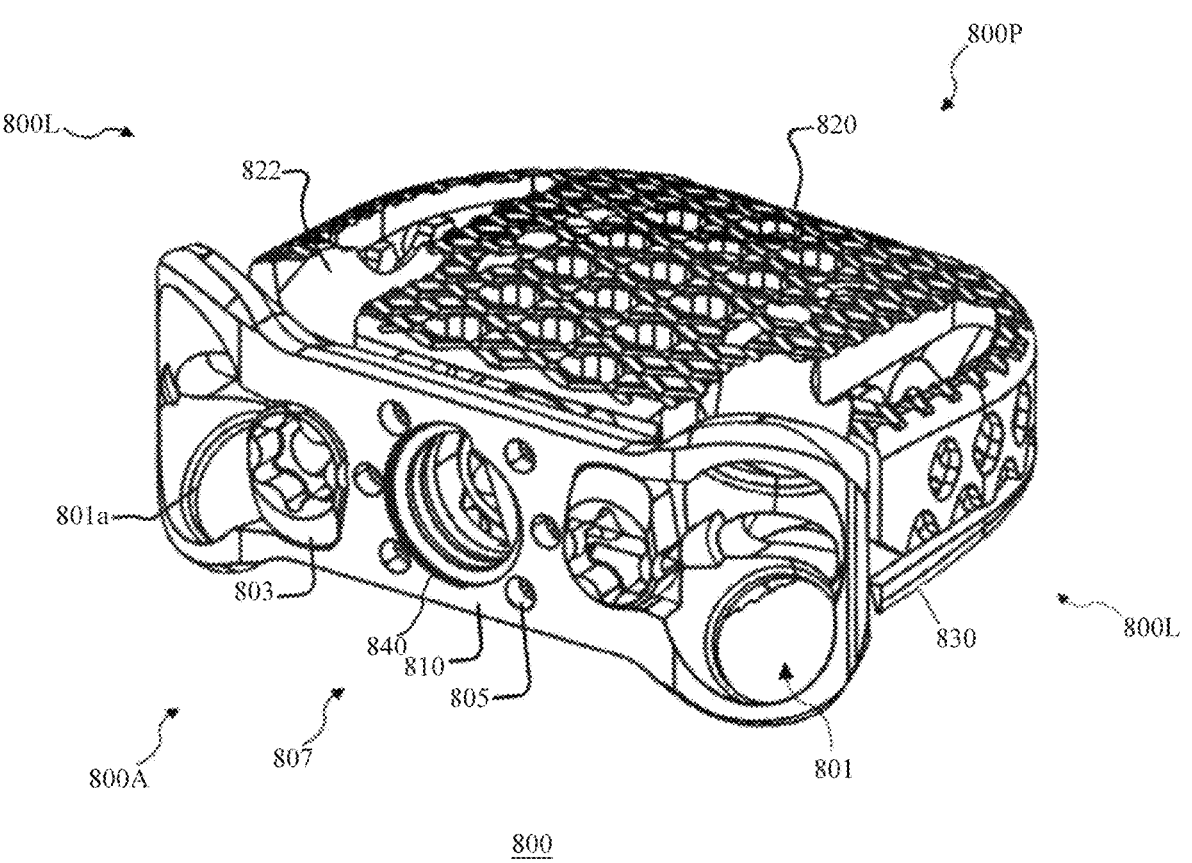
FIG. 1 is a perspective view of an embodiment of an expandable spinal implant including a lateral endplate in accordance with the principles of the present disclosure.

The various bone pin anchoring and installation systems disclosed herein may be configured for use with and/or include an expandable spinal implant. FIG. 1 is a perspective view of an embodiment of an expandable spinal implant 800. Other embodiments of spinal implants are contemplated such as those described in U.S. patent application Ser. No. 17/887,957, herein incorporated by reference in its entirety. Expandable spinal implant 800 includes an endplate 810. In some embodiments, endplate 810 may be configured for use as a medial, anterior, posterior or front endplate depending upon orientation or approach employed and the specific configuration and shape of the implant and the location, side or end to which the endplate is affixed or located with respect to the expandable spinal implant. Expandable spinal implant 800 may also include a top endplate 820 (superior endplate) and a bottom endplate 830 (inferior endplate) as will be explained in further detail below.

Implant 800 may include an anterior side 800a, a posterior side 800p and two opposing lateral sides 8001, for example. Additionally, the outside contours of implant 800 may include a top endplate 820 (superior endplate), bottom endplate 830 (inferior endplate) and a lateral endplate 810 (front endplate), for example. In various embodiments, the top endplate 820 and bottom endplate 830 may collectively define the posterior side 800p (rear side) of implant 800. Lateral endplate 810 may include a plurality of circular bone pin apertures 801, for example. In the example embodiment, four circular bone pin apertures 801 are disclosed although in other embodiments the number of bone pin apertures 801 may be more or less. For example, in some embodiments there may be an additional 5th and 6th bone pin aperture in the medial location of lateral endplate 810. In other embodiments, there may be a total of two bone pin apertures 801 including a left bone pin aperture 801 diagonally projecting over the top endplate 820 and a right bone pin aperture 801 diagonally projecting over the bottom endplate 820.

Lateral endplate 810 may include at least one bone pin lock 803 for preventing one or more bone pins from backing out of endplate 810. For example, bone pin lock 803 may be a rotatable lock that may rotate about 90° between an open position and a closed position. In various embodiments, lateral endplate 810 may include at least one attachment point 805 for connecting implant 800 with a surgical tool. In the disclosed embodiment, a plurality of attachment points 805 are distributed around pin guide aperture 807. In the disclosed embodiment, six attachment points 805 are radially distributed around pin guide aperture 807 although other embodiments may have more or less, e.g., 2, 3, 4, 5, 7 or 8.

Lateral endplate 810 also includes a central aperture 840. In the illustrated embodiment, the central aperture 804 extends through the endplate 810 and provides access to the spinal implant 800 through the endplate 810. The central aperture 840 can be configured to facilitate alignment of a surgical tool with the spinal implant 800. For example the central aperture 840 can be aligned with a component of the spinal implant 800 so that access through the central aperture 840 positions a surgical tool properly in relation to the spinal implant 800.

Figure 2:
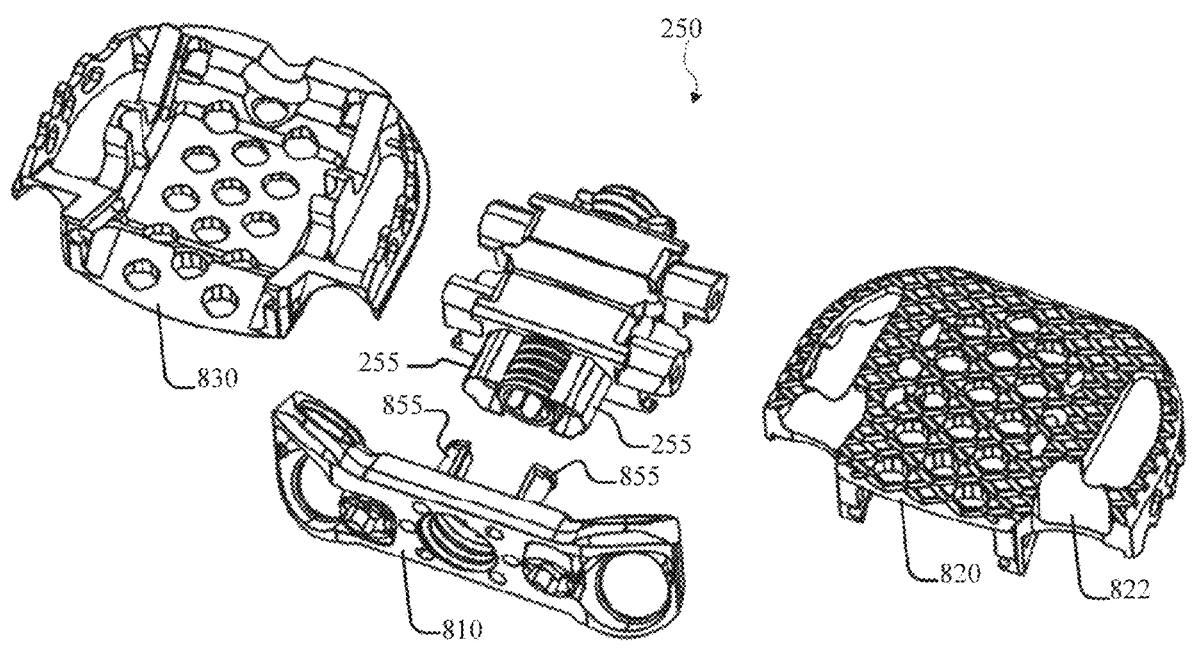
FIG. 2 is an exploded parts view diagram of the embodiment of FIG. 1 in accordance with the principles of the present disclosure.

FIG. 2 is an exploded parts view diagram of the embodiment of FIG. 1 in accordance with the principles of the present disclosure.

As understood best with reference to FIG. 2, lateral endplate 810, top endplate 820, and bottom endplate 830 may be operably coupled to moving mechanism 250. For example, moving mechanism 250 serves as a central attachment location for each of the endplates 810, 820, 830 and each of the endplates 810, 820, 830 may interact independently with moving mechanism 250, for example. In the disclosed embodiment, lateral endplate 810 may be operably coupled to moving mechanism 250 by inserting posts 855 into a corresponding post retaining aperture 255 having a size and shape configured to securely couple the two together. In various embodiments, posts 855 may extend from an inside surface of lateral endplate 810 in a direction towards the posterior side 800*p* of implant 800 and towards moving mechanism 250. In this way, lateral endplate 810 is independently secured to moving mechanism 250 from top endplate 820 and bottom endplate 830, for example.

In the example illustration, bottom endplate 830 may include a bone pin relief 832 for each corresponding bone pin aperture 801. For example, bone pin relief 832 comprises an arcuate channel and/or conical channel defining a portion of the outside surface of endplate 830. In some embodiments, the number of bone pin reliefs 832 may be more or less. For example, a single bone pin relief 832 or three bone pin reliefs 832. In some embodiments, the top endplate 820 may include a first bone pin relief 822 and the bottom endplate 830 may include a second bone screw relief 832 that project oppositely from one another in a diametrically opposed direction.

Figure 3:
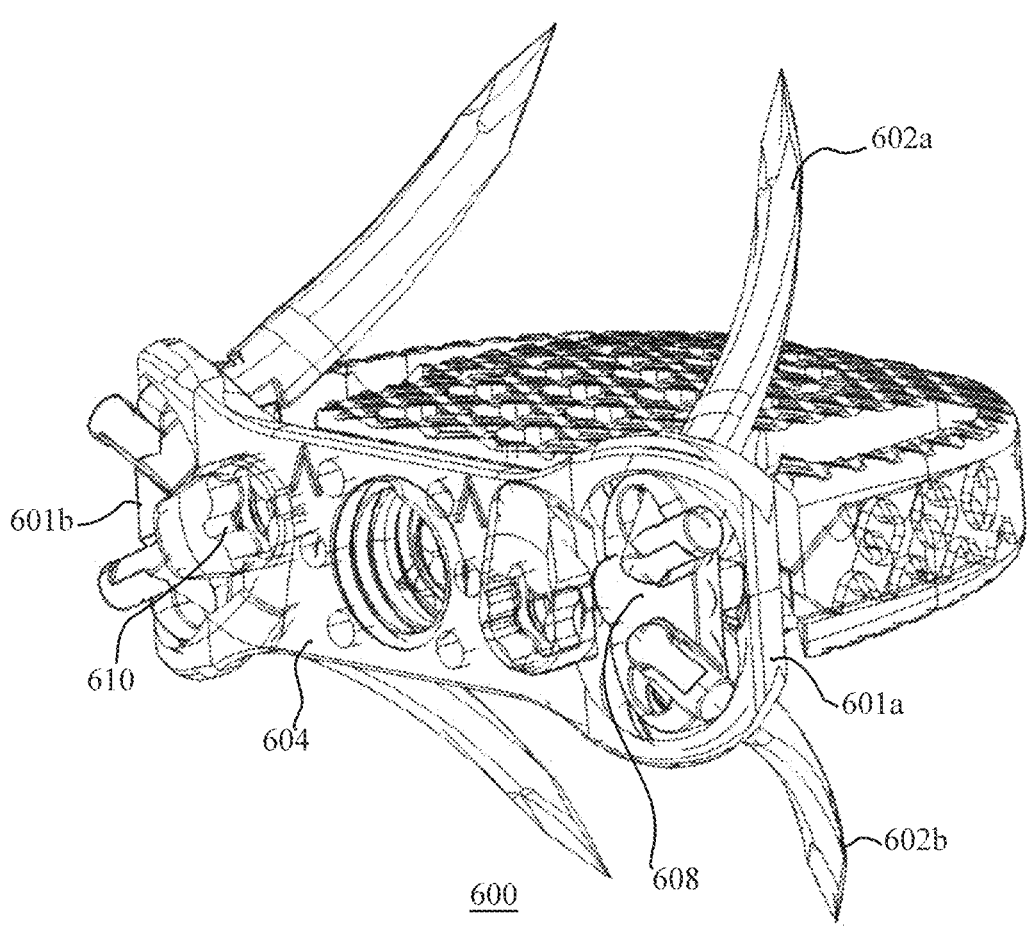
FIG. 3 is a perspective view of the embodiment of FIG. 1 including an anchoring system comprising a plurality of bone pins in accordance with the principles of the present disclosure.

FIG. 3 shows a perspective view of an embodiment of an expandable spinal implant 600. The expandable spinal implant 600 includes an endplate 604 having a first side 601*a* and a second side 601*b*. On first side 601*a*, a connector plate 608, described in further detail herein, is seated in a recess of the endplate 604. The connector plate 608 on first side 601*a* supports a superior bone pin 602*a* and an inferior bone pin 602*b*. A bone pin lock 610 is also located on side 601*a*. The bone pin lock 610 is configured to be rotated in the endplate 604, for example the bone pin lock can be rotated about an attachment point that affixes the bone pin lock 610 to the endplate 604, such as a pin, and can be rotated to at least partially cover the connector plate 608. In this configuration, the bone pin lock 610 can secure the connector plate 608 and the associated bone pins in the endplate 604. As shown in FIG. 3, a complementary connector plate, bone pins and pin lock may be located on side 601*b* and have substantially the same arrangement as those on side 601*a*.

Figure 4:
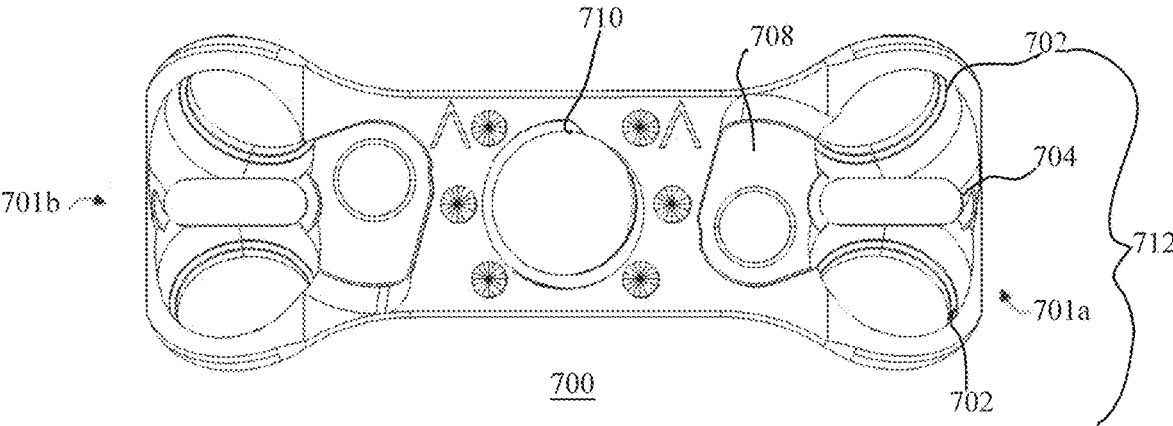
FIG. 4 is an embodiment of an endplate in accordance with the principles of the present disclosure.
Figure 18:
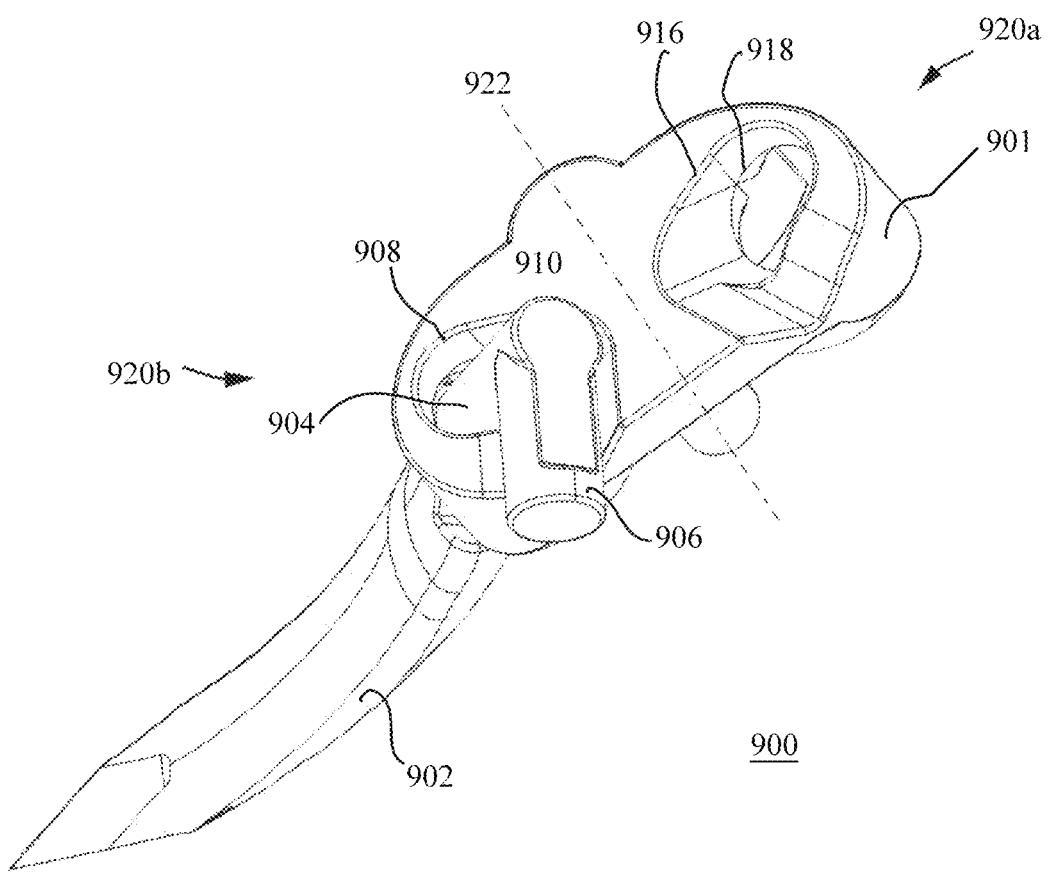
FIG. 18 is a perspective view of an embodiment of a bone pin connector plate in accordance with the principles of the present disclosure.

Referring now to FIG. 4, an embodiment of a lateral endplate of a spinal implant is shown. Lateral endplate 700, has a first side 701*a* and a second side 701*b*. First side 701*a* of the lateral endplate 700 includes two bone pin apertures 702 (although other arrangements are contemplated). Each bone pin aperture 702 is configured to receive a bone pin as described herein. A connector plate seat 704 is located between the two bone pin apertures 702 and is configured to receive a connector plate (see 901 in FIG. 18). The connector plate seat 704 can be a cutout, aperture, seat, groove or other feature of the endplate and can facilitate centering and/or alignment of a connector plate relative to or inside of an indentation of the lateral endplate 700. For example, the connector plate seat 704 can have a geometric configuration corresponding to a feature of a connector plate such as bottom protrusion 914 of connector plate 901, as shown in FIG. 18. Such a geometric configuration can allow the bottom protrusion 914 to be received in the connector plate seat 704. Additionally, each of the bone pin apertures 702 may have a ring-shaped perimeter, that may, collectively with the connector plate seat 704, form a receiving region 712 configured to receive a connector plate. For example, the receiving region 712 can have a geometric configuration similar to that of inferior surface 912, shown in FIG. 19. Second side 701*b* of the lateral endplate 700 may include a substantially similar arrangement of bone pin apertures and/or connector plate seat as first side 701*a*. Lateral endplate 700 also includes one or more bone pin lock seats 708 having a geometric configuration configured for receiving a bone pin lock (see 610 in FIG. 3). Additionally, a central alignment aperture 710, discussed in more detail later, is included in the lateral endplate 700 and may be configured to facilitate aligning a spinal implant with a surgical tool.

Figure 5:
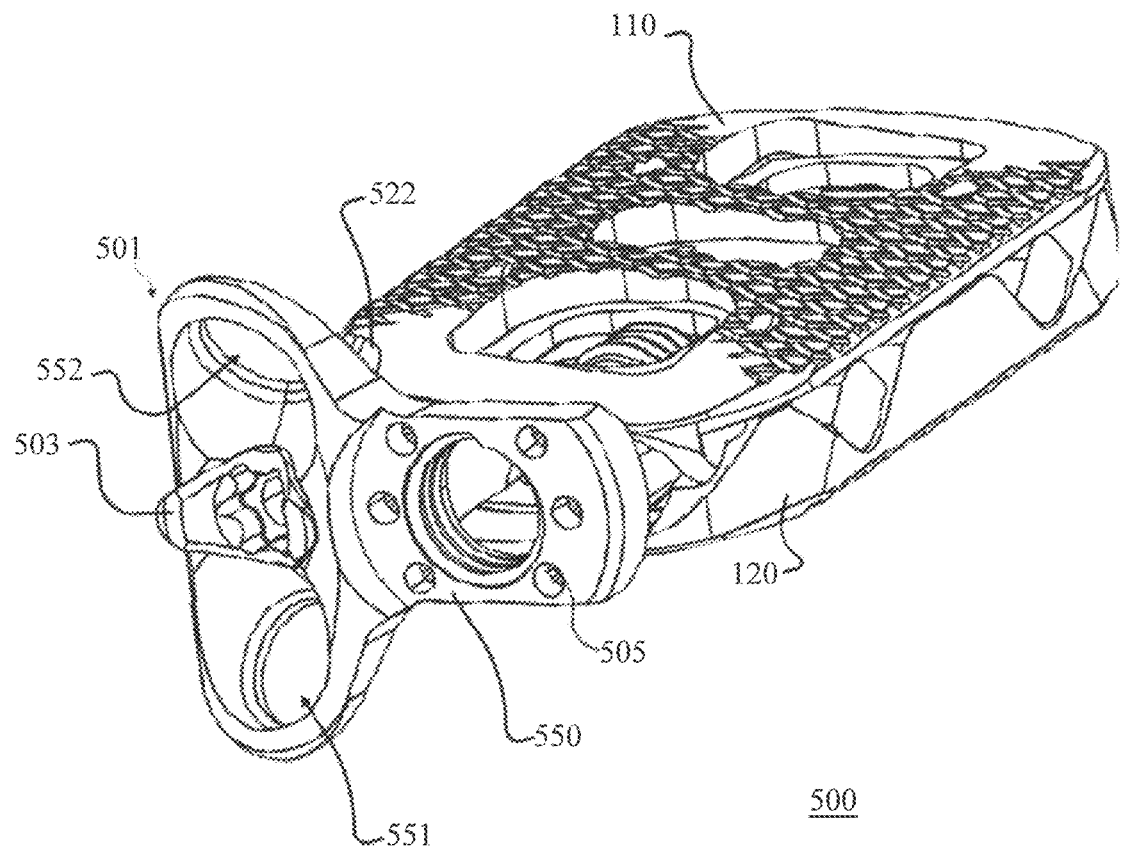
FIG. 5 is an alternative embodiment of a spinal implant including a lateral endplate in accordance with the principles of the present disclosure.

FIG. 5 shows an alternative embodiment of a lateral endplate 501 coupled to an embodiment of an expandable spinal implant. Implant 520 may have the same, similar, and/or substantially the same features and functionality as the various spinal implants disclosed herein. Accordingly, duplicative description will be omitted or only briefly described. The illustrated embodiment of FIG. 5 has an inferior bone pin aperture 551 and a superior bone pin aperture 552 that is vertically aligned with inferior bone pin aperture 551. There is a bone pin relief 522 in top end plate 150 located behind superior bone pin aperture 522. A similar bone pin relief may be located behind inferior bone pin aperture 551 in bottom endplate 120. Proximal plate 550 is coupled to implant 520 either rigidly or pivotally to allow for lateral movement, vertical and/or rotational movement. In addition, bone pin apertures 551 and 552 are oriented to one lateral side of proximal plate 550. In other embodiments bone pin apertures 551 and 552 can be vertically aligned with proximal plate 550. For example, bone pin aperture 551 can be located vertically below proximal plate 550 and bone pin aperture 552 can be located vertically above proximal plate 550. FIG. 5 also shows a plurality of attachment points 505 on proximal plate 550 for attachment of spinal implant 520 to a surgical tool.

In other embodiments proximal plate 550 may be omitted in favor of an alternate connection between lateral endplate 501 and spinal implant 520. For example, a threaded connection between one or more surfaces on the lateral endplate 501 and the spinal implant 550 may connect the two components. Alternatively, the attachment points 505, discussed above, can be located on a surface of spinal plant 520 instead of on the proximal plate 550 in embodiments in which proximal plate 550 is omitted.

A bone pin lock 503 is shown in the illustrated embodiment and can be rotated to lock one or more bone pins in place. In some embodiments bone pin aperture 551 and 552 may each have a corresponding bone pin lock. In alternative embodiments there may be one bone pin lock corresponding to each bone pin aperture and/or each bone pin. In some embodiments, each bone pin aperture may be configured to accommodate one bone pin. In alternative embodiments, each bone pin aperture may be able to accommodate two or more bone pins. In some embodiments, each bone pin aperture may be configured to accommodate two or more bone pins connected by a bone pin connector plate, as disclosed herein.

The various bone pin installation systems disclosed herein may include one or more surgical tools for implant component insertion, deployment and manipulation of various system components into an interbody space of a patient. Various surgical tools for insertion of a spinal implant are contemplated, such as those in U.S. patent application Ser. No. 17/307,706 incorporated herein by reference in its entirety.

Figure 6:
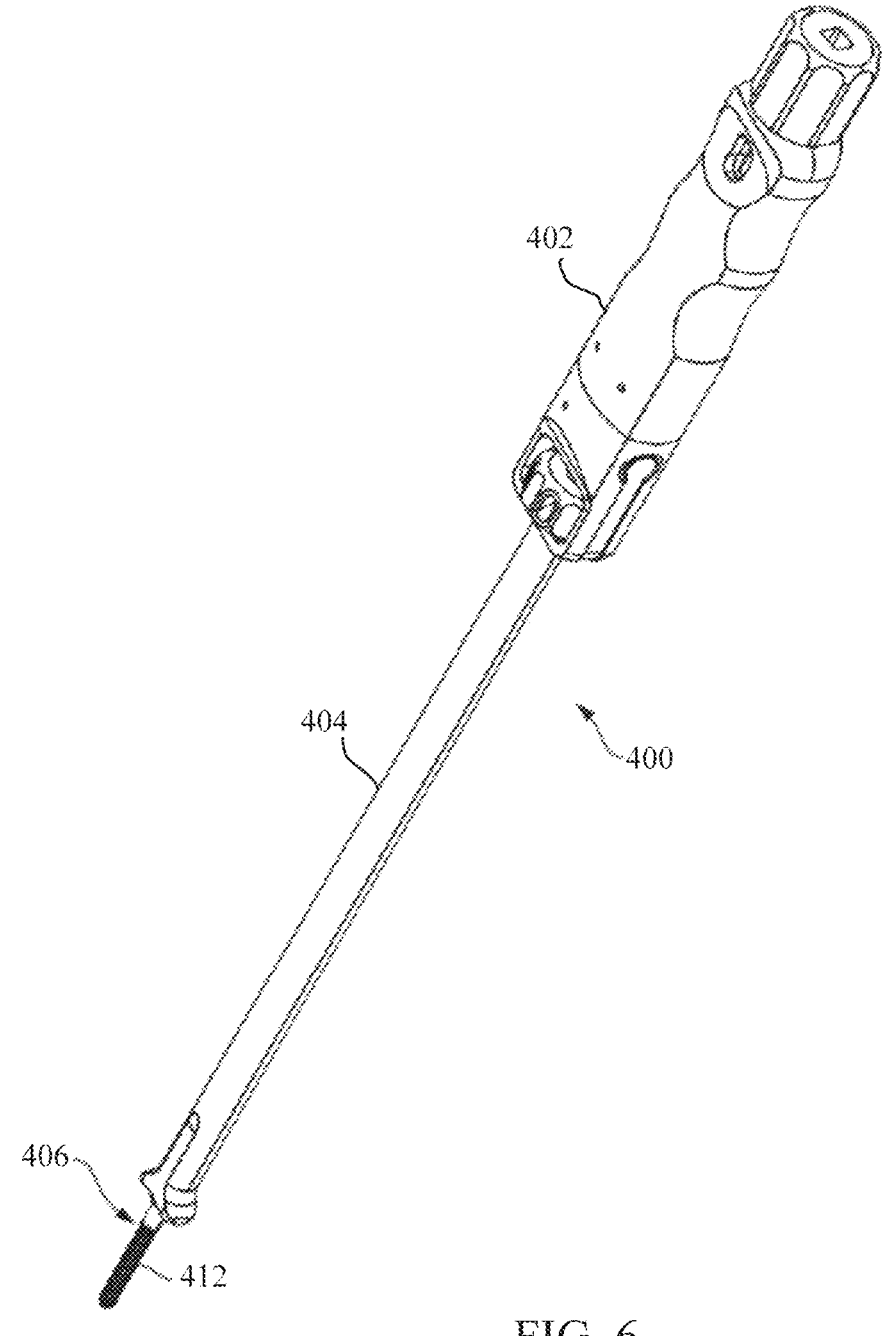
FIG. 6 is an embodiment of a surgical tool for adjusting and inserting various implants in accordance with the principles of the present disclosure.

FIG. 6 shows an embodiment of a first surgical tool 400 for inserting and/or positioning a spinal implant 100 e.g., between vertebral bodies during surgery or another procedure. The first surgical tool 400 includes a handle 402 and a shaft 404. The shaft 404 includes a tip 406 having a threaded portion 412. The threaded portion 412 may be configured to separably connect to a spinal implant such that spinal implant may be securely attached to first surgical tool 400 during insertion of the spinal implant in situ and then detached from the spinal implant following insertion.

Figure 7:
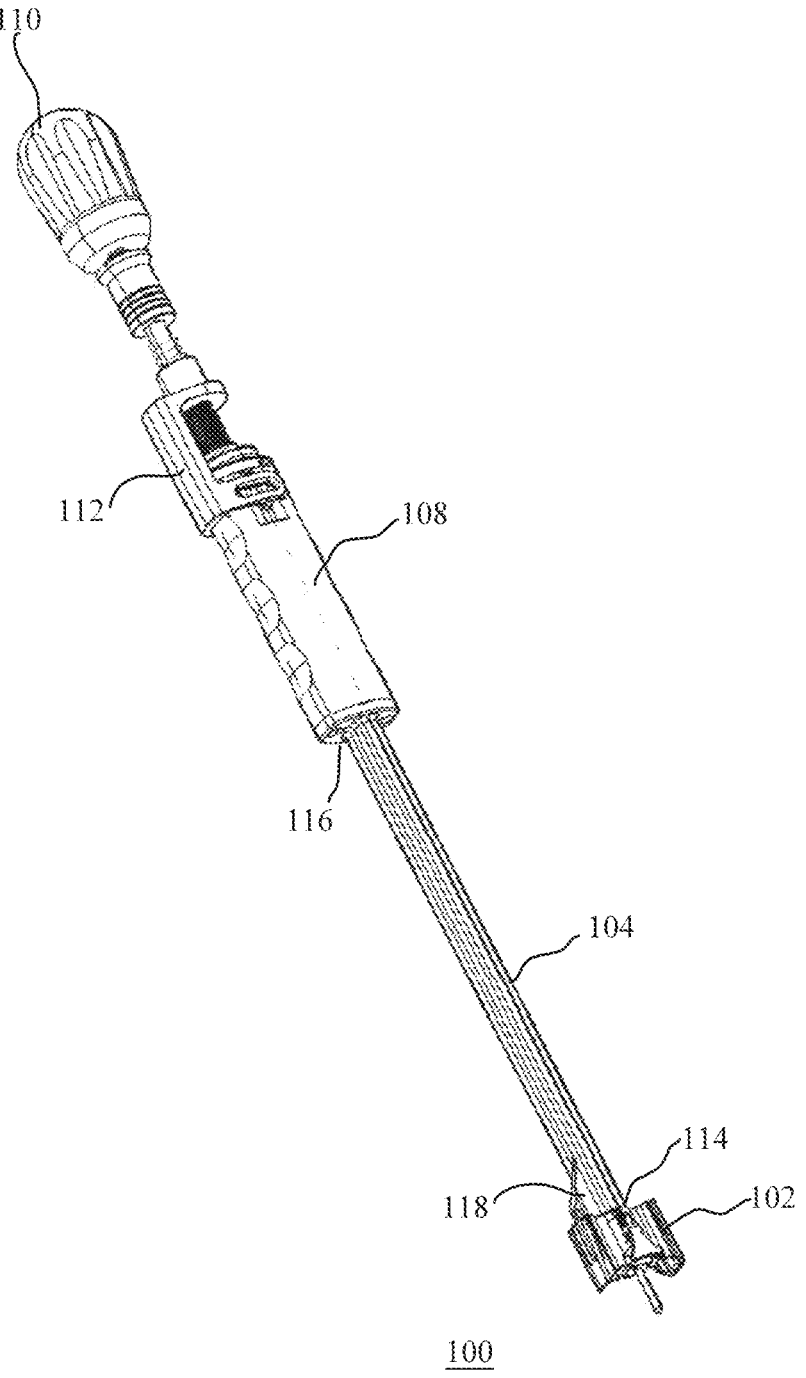
FIG. 7 is an embodiment of another surgical tool for inserting and installing a bone pin anchoring system in accordance with the principles of the present disclosure.
Figure 8:
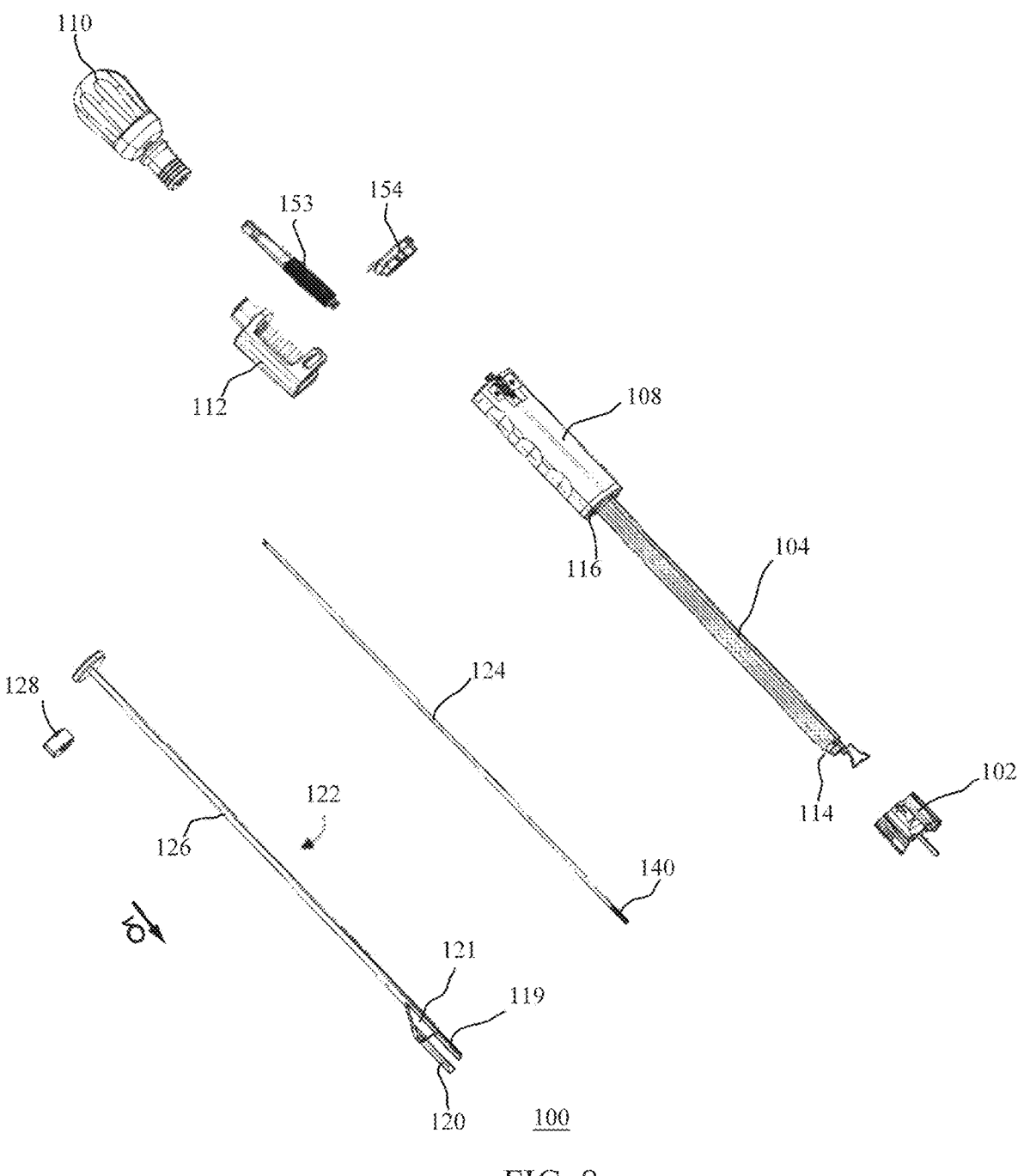
FIG. 8 is an exploded view of the embodiment of FIG. 7 in accordance with the principles of the present disclosure.

FIGS. 7 and 8 show an embodiment of a second surgical tool 100. Other embodiments of a second surgical tool are contemplated. The first surgical tool 400 can be used in conjunction with a second surgical tool 100. For example, the first surgical tool 400 may be used for inserting of a spinal implant and the second surgical tool may be used for deploying bone pins and/or bone pin anchor systems, into the spinal implant via surgical tool 100. The illustrated embodiment includes a shaft 104 having a proximal end 116 relatively near handle 108 and a distal end 114 downstream of proximal end 116. In the illustrated embodiment, a guide 102 is located on the distal end 114 of the shaft 104. The guide 102 may be separably connected to the shaft 104. For example, in some embodiments, the distal end 114 of the shaft 104 may include a threaded portion configured to connect with a threaded surface on the guide 102. In alternative embodiments the guide 102 may be connected to the shaft 104 by way of other fasteners such as pins or screws.

In addition, the illustrated embodiment includes a pushing element 122 having a longitudinal stem 126 and a forked end 118. The forked end 118 is configured to be received in an anchor aperture 1514 (shown best in FIG. 15) during impaction of bone pins and/or bone anchors. The guide 102 also includes a guide rod 106 for facilitating in lining up the bone pin anchor systems properly with a spinal implant in order to facilitate proper impaction. For example, such that when impacting the bone pins these pins will extend through the corresponding apertures of the spinal implant as will be explained in further detail below. The guide 102, pushing element 122, and fork 112 are discussed in more detail below.

The illustrated embodiment in FIG. 8 also includes a stop axis 124. The stop axis 124 includes a threaded portion 140 for attaching another component of a second surgical tool, such as guide 102. The stop axis 124 may be housed by the shaft 104 and be used to manipulate a stop (discussed in more detail below) on the second surgical tool 100.

The handle 108 encloses a volume and at least a portion of the shaft 104 may be received in the handle volume. In some embodiments the handle 108 may enclose a portion of the shaft such as proximal end (116) while another portion of the shaft remains unenclosed such as distal end (114). In the illustrated embodiment, the handle 108 includes a removable end cap 154. A fork 112 is separably insertable within and/or connectable to the handle 108. The fork includes a fork axis 153. A first adjustment knob 110 is located upstream of the fork 112 adjacent to the proximal end. The first adjustment knob 110 may be separably connected to the fork 112 such as by way of a threaded connection to fork axis 153. The separable connection of the fork 112 and the first adjustment knob 110 allows for access to a handle aperture (see 1904 in FIG. 9) on the handle 108 and/or handle end cap 154 i.e., the first adjustment knob 110 and fork 112 may be removed so that a pushing element 122 or other component of the second surgical tool 100 may be fed through a handle aperture.

Figure 9:
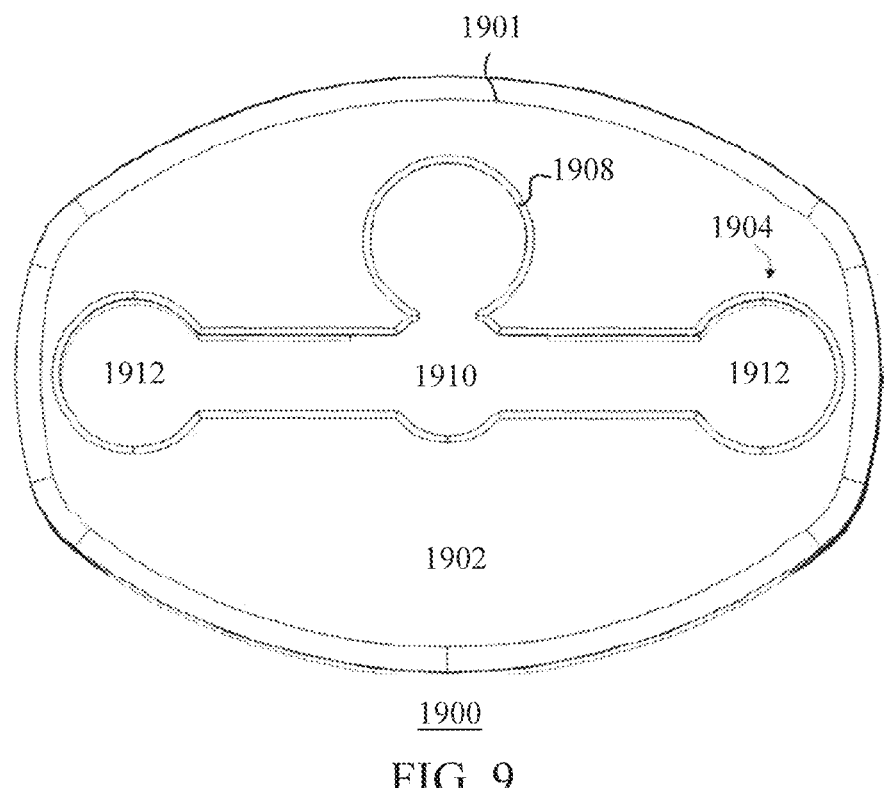
FIG. 9 is a top-down view of a handle of the surgical tool of FIG. 7 in accordance with the principles of the present disclosure.

Referring now to FIG. 9, a top-down view of a second surgical tool 1900, like that shown in FIG. 7 is shown. In FIG. 9 the fork 112 and first adjustment knob 110 from the second surgical tool 100 of FIG. 7 have been removed for ease of understanding the remaining components. The second surgical tool 1900, includes a handle 1901, having a top surface 1902 with a handle aperture 1904. In the illustrated embodiment, the handle aperture 1904, has a T-bone, dog bone or other similar shape in order to allow the forked end of a pushing element to be fed through apertures shown in the handle 1901 of FIG. 9. For example, the illustrated embodiment shows the handle aperture 1904 with two bulbous ends 1912 linked by a linear middle portion 1910. The bulbous ends 1912 have a different shape than the linear middle portion 1910 to accommodate a forked end of a pushing element e.g. forked end 118 in FIG. 8. The handle 1901 also includes a stop axis aperture 1908 so that a stop axis (not shown) may be fed through the handle to a distal end of the second surgical tool 1900 proximal to a guide (e.g., guide 102 in FIG. 8). The stop axis can be a rod with a threaded end for receiving a stop. The stop axis and the stop may be used to position a stop configured to control impaction depth of the guide during impaction of a bone pin anchoring system.

Figure 10:
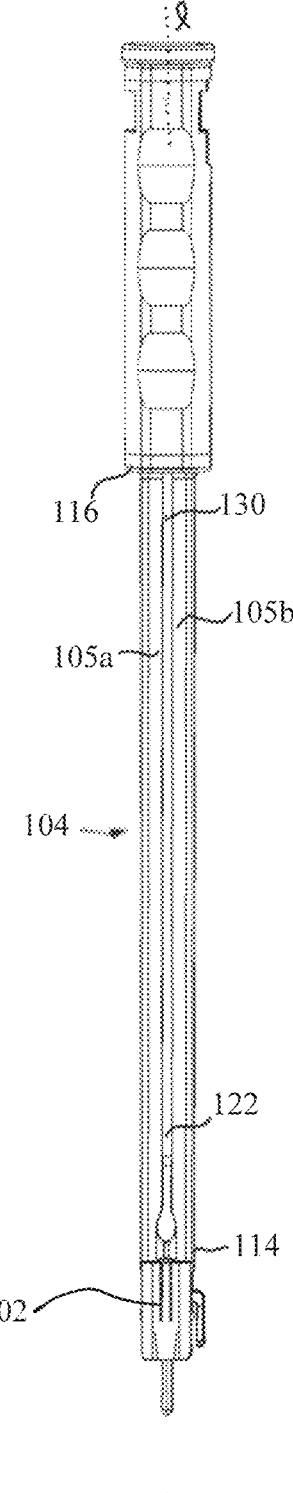
FIG. 10 is a side view of the surgical tool of FIG. 7 in accordance with the principles of the present disclosure.

Referring now to FIG. 10, a second surgical tool 100 includes a shaft 104 having a first wall 105a and a second wall 105b opposite first wall 105a. The spacing between first wall 105a and second wall 105b forms a shaft aperture 130 extending along the longitudinal axis, $\lambda$, of the shaft 104 between a proximal end 116 and distal end 114 of the shaft 104. The shaft aperture 130 may be configured to at least partially receive a component of the second surgical tool 100 such as a pushing element 122 and/or a stop axis (not shown). In the illustrated embodiment, the pushing element 122 can be seen between first wall 105a and second wall 105b. For example, the pushing element 122 and/or stop axis can be fed through one of the handle apertures discussed previously and received in the shaft aperture 130. The shaft aperture 130 guides the pushing element 122 and/or stop axis by allowing movement along the longitudinal axis of the shaft 104 while limiting horizontal movement in the transverse direction of the shaft 104.

Figure 11:
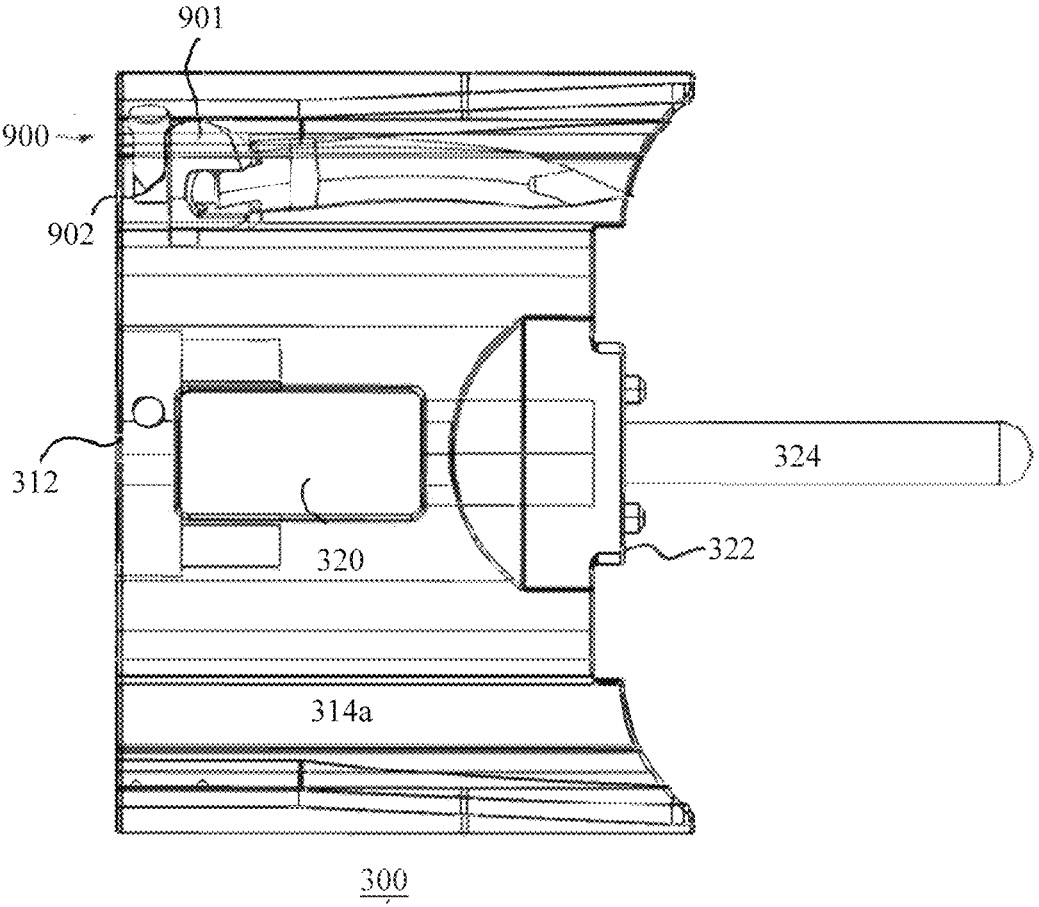
FIG. 11 is a side perspective view of an embodiment of a guide in accordance with the principles of the present disclosure.

FIG. 11 shows an embodiment of a guide 300. The guide 300 may be attached to a second surgical tool such as that shown in FIG. 10 (see guide 102 attached to second surgical tool 100). The guide 300 includes a second face 322 opposite a first face 312 having a guide rod 324. The guide rod 324 may be configured to be received in a portion of a spinal implant in order to facilitate alignment of the guide 200 with the spinal implant. For example, the guide rod 324 may be received in a central aperture of a spinal implant. This further facilitates alignment of the guide 200 with the spinal implant and aids in proper bone pin placement in the implant. A bone pin anchor system 900 including a bone pin 902 and a connector plate 901 is shown seated in the guide 300. In some embodiments, the guide may include a window 320, providing access to the interior of the guide 300. The window 320 can be seen on elongated side 314a of the illustrated embodiment.

Figure 12:
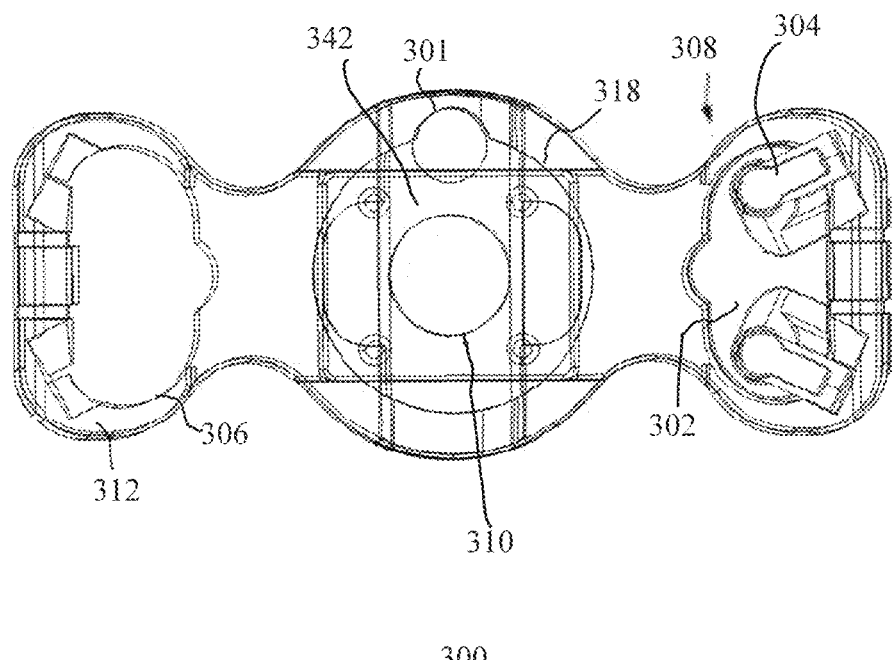
FIG. 12 is a top-down view of an embodiment of a guide in accordance with the principles of the present disclosure.

Referring to FIG. 12, a top-down view of a guide 300 is shown. In some embodiments, the guide 300 may include a threaded surface 301, which may utilize threads in order to attach the guide 300 to a threaded portion of a second surgical tool. For example, the threaded surface 301 may be configured to connect the guide 300 to a threaded portion of a stop axis on a second surgical tool. The guide 300 includes a first face 312 having one or more anchor apertures 306 configured to receive one or more embodiments of an anchoring system 308. The location of the anchor apertures 306 on the first face 312 may correspond to the location of regions (e.g., regions formed collectively by the bone pin apertures 702 and connector plate seat 704 in FIG. 4) on an endplate and be of a similar geometry to such regions. This correspondence in size and shape facilitates the deployment of one or more bone pins and/or bone pin anchoring systems into the apertures of the endplate of a spinal implant using the second surgical tool. In the embodiment illustrated in FIG. 12, the guide 300 also includes a central alignment aperture 318 on first face 312. Nested inside of central alignment aperture 318 is a surface 342 having a shaft aperture 310. The central alignment aperture 318 may have a diameter large enough to accommodate at least one prong (e.g., prong 119 in FIG. 8) on a pushing element (e.g., pushing 122 in FIG. 8). The shaft opening 310 may have a diameter large enough to receive a portion of a shaft of a second surgical tool.

Figure 13:
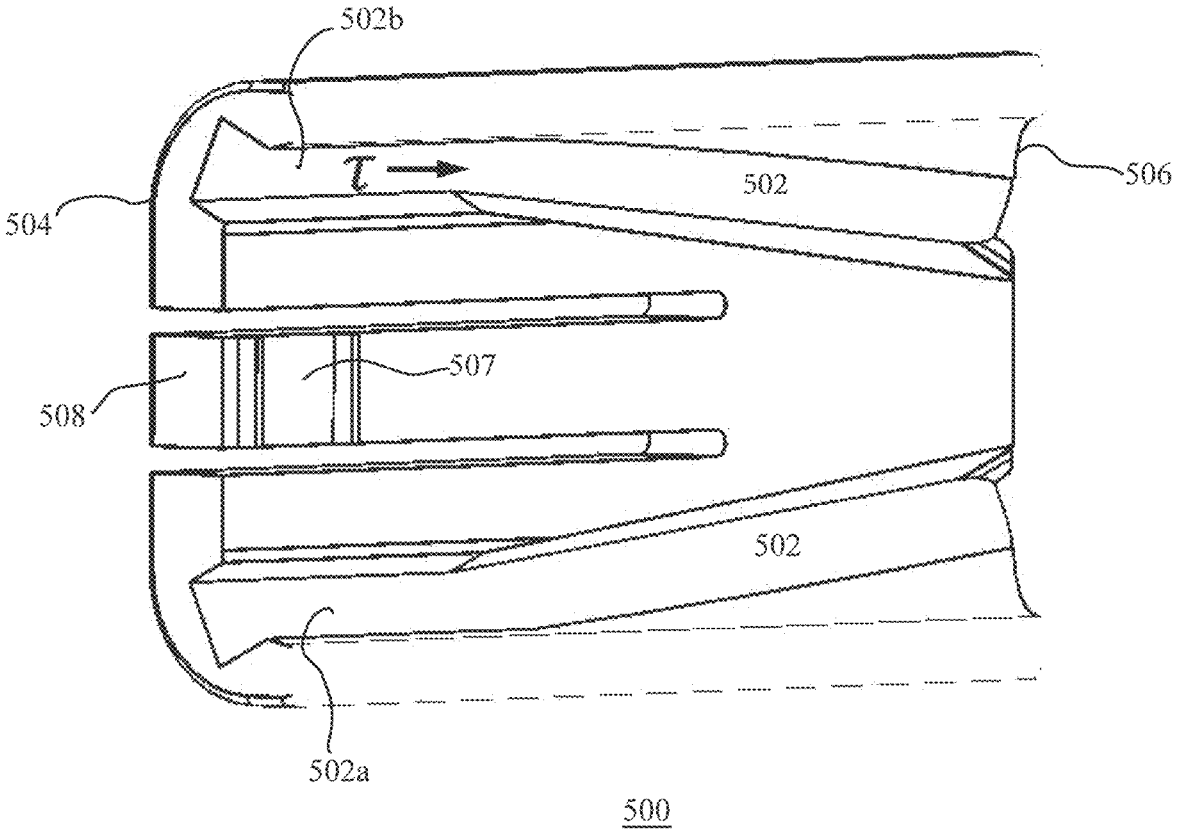
FIG. 13 is a section view of a portion of an embodiment of a guide in accordance with the principles of the present disclosure.

FIG. 13 shows a section view of an embodiment of a guide 500. In the illustrated embodiment, one or more channels 1102 are shown on an interior surface located inside the one or more anchor apertures (see 306 in FIG. 12) on the guide 500. The channels 1102 are configured so that when the bone pins (and connector plate) (as shown in FIG. 11) are inserted in the one or more anchor apertures a support arm (e.g., 504 in FIG. 17A) of each bone pin is aligned within a corresponding channel 502. The one or more channels 1102 run between a first face 1104 and second face 1106 of the guide. In some embodiments, there is a channel 1102 corresponding to each bone pin seated within the connector plate i.e., if a connector plate (e.g. 901 in FIG. 11) contains two bone pins there may be two channels 1102 in the corresponding anchor aperture, e.g., an upper channel 1102 and a lower channel 1102 that diverge in different directions as shown in the cross section drawing of FIG. 13. In alternative embodiments, the number of channels and corresponding bone pins can differ. In many embodiments each bone pin may have a corresponding channel 502, e.g., three bone pins and three corresponding channels, four bone pins and four corresponding channels.

The channels 1102 define a trajectory, denoted by t configured to allow the support arm (1104 in FIG. 17A) of the bone pins to rotate therein. For example, FIG. 13 has two channels 502, each channel 1102 may be configured to receive the support arm 504 of one corresponding bone pin. The trajectory of each of the channels 1102 is relatively straight along a first portion thereof that is close to the anchor aperture (306 in FIG. 12) and then gradually converges inwardly along a second portion thereof that is toward the other channel 1102 so that the space between the two channels decreases between the first face 1104 and second face 506. In various embodiments, this configuration of the support arm 504 of a first bone pin to rotate in a first channel 1102*a* in a clockwise direction relative to the medial axis 518 of the bone pin (see FIGS. 17A and 17B). Likewise, the second bone pin rotates in a second channel 1102*b* in a counter-clockwise direction relative to the medial axis 518 causing the distal ends of the first and second bone pins to diverge relative to a central axis of a connector plate. For example, during impaction the channels cause the corresponding bone pins to splay outwards relative to the central axis of the connector plate. In the illustrated embodiment, the trajectories of the two channels 1102*a* and 1102*b* are substantially symmetrical so that each of the two bone pins diverges in the same manner (or a similar manner) as the other bone pin but in an opposite direction (or a different direction). In various embodiments the two bone pins may diverge an equal amount, and in other embodiments the two bone pins may diverge a different amount, e.g., depending on the particular needs of the patient's anatomy and the orientation of the bone pin apertures on the endplate of the implant. In various embodiments, the channels 1102*a*. 1102*b* allow for precise manipulation of the pins divergence and rotation thereof during an installation procedure and such divergence and rotation may facilitate anchoring of the bone pins into a bony structure. The control the guide 500 imparts over the bone pins via the channels 1102 facilitates a surgeon in installing the bone pins in a manner that promotes stability of an associated spinal implant. Additionally, the curved nature of the bone pins and the divergence of the bone pins during an installation procedure may also increase the retention of the bone pins in patient anatomy relative to straight bone pins and/or bone pins that do not diverge during impaction. In this way, embodiments in accordance with the principles of this disclosure improve upon systems of the prior art.

The guide 500 may be outfitted with a deflector tab 1108 adjacent to each of the anchor apertures. The deflector tab 1108 may be configured to temporarily retain and orient the connector plate relate to the guide 500 immediately prior to impaction. For example, the deflector tab 1108 may temporarily retain the connector plate and bone pins during an insertion and alignment process prior to impaction of the bone pins. In addition, each deflector tab 1108 has a corresponding groove 1107 on an inner surface of each of the connector plate apertures configured to position the connector plate within the connector plate aperture. When the bone pins and connector plate are loaded into the guide 500 the deflector tab 1108 extends in a direction, e.g., outwardly from a longitudinal axis of a second surgical tool, so as to allow the connector plate (with bone pins) to pass through the connector plate aperture and align with the groove 1107 so that the bone pins and connector plate sit within the guide 500 securely and with the proper orientation for impaction. In this way, the deflector tab 1108 deflects outwardly and then snaps back into place. The unique geometrical arrangement shown in the example embodiment then allows the forward motion of the connector plate and bone pins during an impaction process.

Referring back to FIG. 8 an embodiment of a pushing element 122 is shown. In the illustrated embodiment the pushing element 122 includes a first prong 119 and a second prong 120 connected by a bridge 121 therebetween. In this embodiment, the first prong 119 is formed from the tip of the stem 126 of the pushing element 122. That is to say that the first prong 119 is coaxially aligned with the longitudinal axis of the stem of the pushing element 122 and the second prong 120 is offset to the side of the longitudinal axis of the stem. The second prong 120 extends off of the bridge 121 in a direction, δ, and is substantially parallel to the first prong 119. In some instances, such as during impaction, the first prong 119 may partially extend within a central alignment aperture such as central alignment aperture 318, shown in FIG. 12. Likewise, the second prong 120 may extend partially within a connection plate aperture such as connection plate aperture 308, also shown in FIG. 12 so that the bridge straddles a portion of connection plate 300 between the central alignment aperture 318 and connection plate aperture 308.

Figure 14:
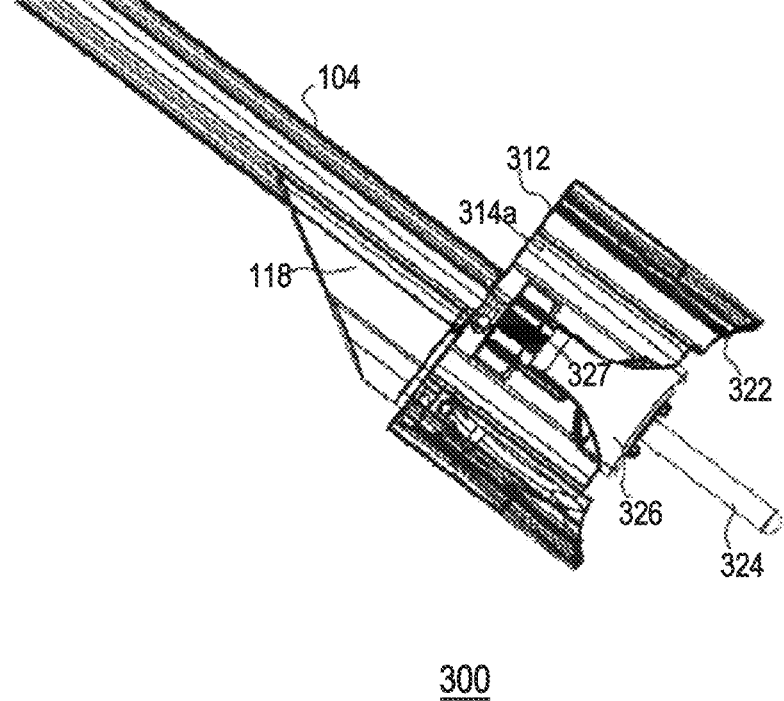
FIG. 14 is a zoomed in view of the distal end of the surgical tool of FIG. 7 in accordance with the principles of the present disclosure.

Referring now to FIG. 14, a guide 300 includes a first elongated side 314*a* and a second elongated side (not shown) opposite first elongated side 314*a*. A first face 312 and a second face 322 opposite the first face 312 are shown. First face 312 abuts the shaft 104 of a second surgical tool. The shaft has a forked end 118 located near enough to first face 312 so as to extend at least partially within an aperture on first face 312. Second face 322 includes a guide rod 324.

In the illustrated embodiment a stop 326 is located on the first elongated side 314*a* of guide 300 and is connected to a stop shaft 327. The stop shaft 327 may extend alongside a shaft or within a shaft aperture of a second surgical tool and be connected to a first adjustment knob upstream of the guide 300 e.g., near a handle of a second surgical tool. The stop 326 may be connected to the stop shaft 327 by a threaded connection. For example, the stop 326 can be threadably connected to an end of stop shaft 327 which may extend partially within the guide. In various embodiments, a user can use a second adjustment knob to extend and retract the stop 326 between a first position and a second position. For example, a user can press a button on a second surgical tool to release the second adjustment knob (see 1614 in FIG. 16). The user can then turn the second adjustment knob in a clockwise or counterclockwise direction to extend the stop shaft 327 to a first position.

The stop may include a planar surface, which may be configured to provide close fit contact between the planar surface and a fixed structure e.g., a vertebrae or other bony structure. When the guide is positioned in situ, the user can extend the stop so that the planar surface is in contact with a nearby bony structure, and in turn, the nearby bony structure provides a stabilizing surface for the guide to rest on, e.g., during impaction of the bone pins. Additionally, the contact between the stop and the nearby bony structure limits the depth of insertion of the second surgical tool into an interbody space.

Figure 15:
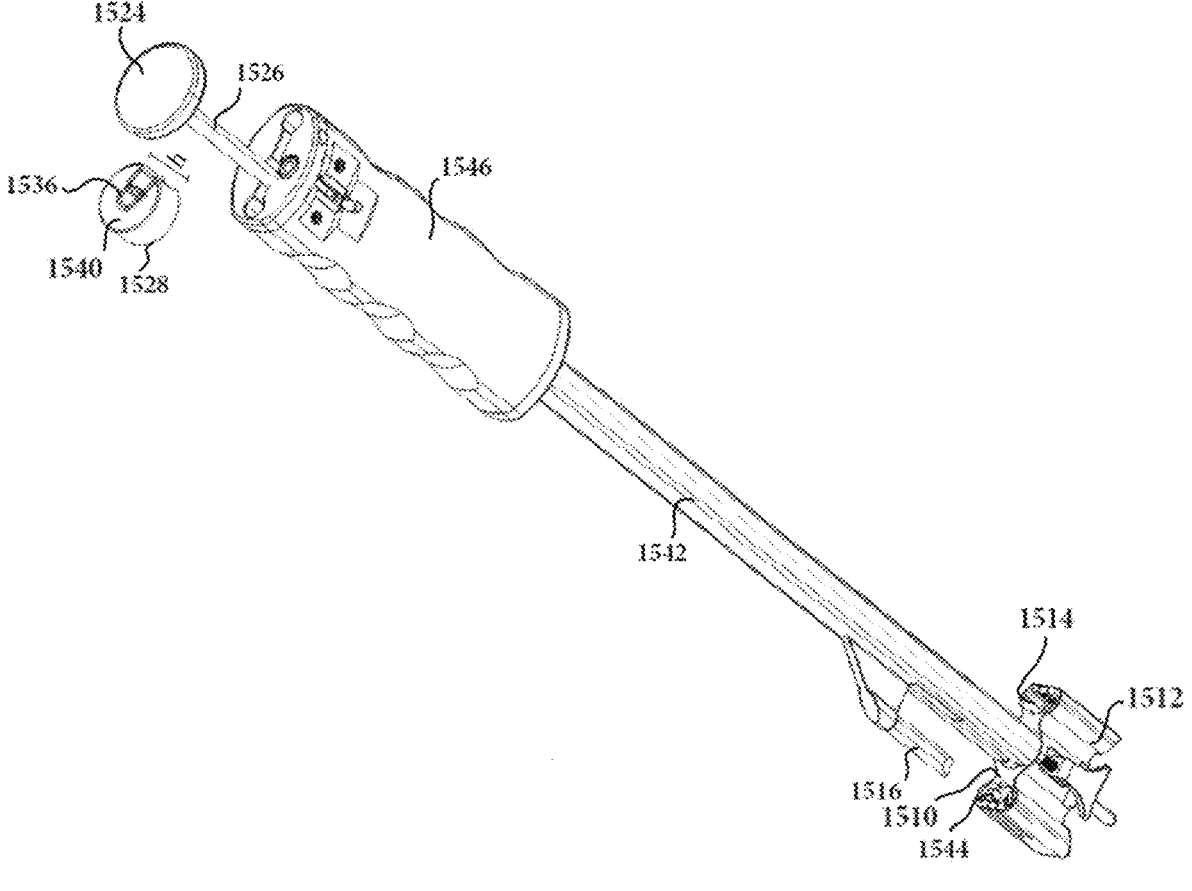
FIG. 15 is an alternative perspective view of an embodiment of another surgical tool in accordance with the principles of the present disclosure.

FIG. 15 shows an embodiment of a pushing element 1542 on an embodiment of a second surgical tool 1500. The pushing element 1542 includes a stem 1526 having a proximal end and a distal end. One or more prongs 1516 are located on the distal end of the stem 1526. A knob 1524, e.g., a substantially flat headed knob 1524 is located on the proximal end of the stem 1526 and is configured to sustain an impaction force from a striking tool such as a hammer, piston, or other blunt instrument. The stem 1526 of the pushing element 1542 may be at least partially disposed inside a shaft aperture. A guide 1512 is connected to an end of the second surgical tool 1500. The guide 1512 may contain one or more bone pin anchoring systems 1544 received in one or more anchor apertures 1514 on a first surface 1510 of the guide 1512. FIG. 15 shows one of the anchor apertures 1514 void of an anchoring system 1544. This is merely for ease of understanding and both anchor apertures 1514 in FIG. 15 are configured to receive an anchoring system 1544. Additionally or alternatively, the one or more prongs 1516 can extend at least partially into the one or more anchor apertures 1514 of the guide 1512 so that the tip of one or more of the prongs 1516 are in contact with a portion of the one or more bone pin anchor systems 1544.

During impaction of the one or more bone pin anchor systems 1544, a user can apply a force to the substantially flat head 1524 of the pushing element 1542 and this force may be transferred by contact of the pushing element 1542 by way of the prongs 1516 with the one or more bone pin anchor systems 1544 thereby creating a successive chain of forces driving impaction of the one or more bone pin anchor systems 1544.

FIG. 15 also shows an embodiment of a wedge 1528. The wedge 1528 has a height h and a substantially semi-circular cross section 1540. The wedge 1528 also includes a first surface 1536. The first surface 1536 forms a groove configured to be received around the stem 1526 of the pushing element 1542 so that the wedge 1528 may be securely attached to the stem 1526. In some embodiments, the wedge 1528 is placed around an end of the stem 1526 located upstream of a handle 1546. The wedge 1528 limits the extension of the pushing element 1542 by height h during impaction and thereby limits the depth at which the bone pin anchor systems 1544 are impacted. This configuration also allows removal of the wedge 1528 and utilization of wedges 1528 having different heights or thicknesses so that a user may alter the impaction depth.

Figure 16:
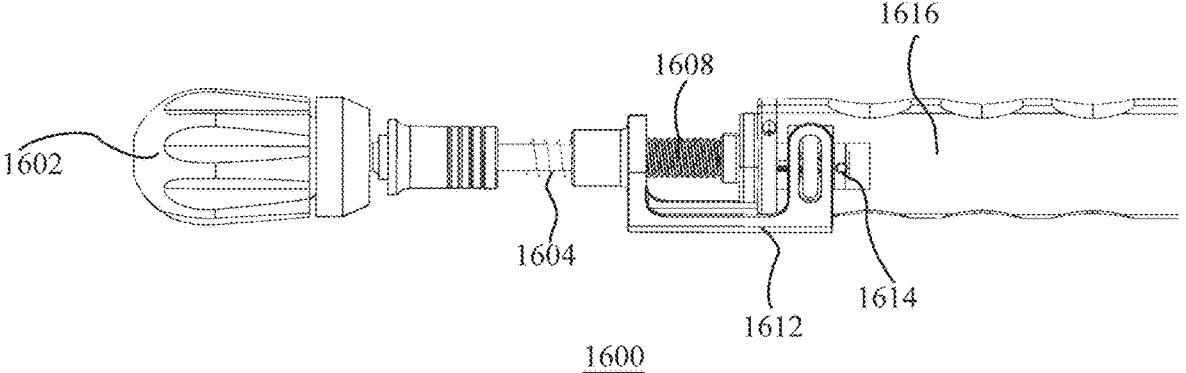
FIG. 16 is a zoomed in view of a portion of an embodiment of another surgical tool in accordance with the principles of the present disclosure.

FIG. 16 shows a portion of a proximal end of an embodiment of a second surgical tool 1600 utilizing a different end for impaction of bone pins. The illustrated embodiment includes a fork 1612 that is connected to a handle 1616 of the second surgical tool 1600. In the example embodiment, fork 1612 is a C-shaped fork. The fork 1612 may be separably connected to the handle 1616 via a threaded connection 1608 or other suitable means. A rotatable adjustment knob 1602 is located upstream of the fork and defines the proximal end of the tool. The adjustment knob may be connected via a threaded connection to the fork 1612 and may be removable from the fork 1612 as discussed previously. The separability of the fork 1612 and adjustment knob 1602 may allow for replacement by another tool such as a pushing element to one or more handle apertures. A user may turn the adjustment knob 1602 in order to gradually impact one or more bone pin anchor systems or to finish the impaction thereof after usage of a hammer applying a blunt force as explained above. In some embodiments the adjustment knob 1602 may compress a spring 1604, which applies a force to a pushing element in order to impact one or more bone pin anchor systems. Additionally, or in the alternative, the adjustment knob 1602 may tighten a threaded connection between a pushing element and the fork 1612 and cause the pushing element to extend so as to impact the one or more bone pin anchor systems. In various embodiments, the adjustment knob 1602 and fork 1612 can also be used to complete the final portion of impaction of the bone pin anchor systems following an initial partial impaction completed with a pushing element.

Figure 17A:
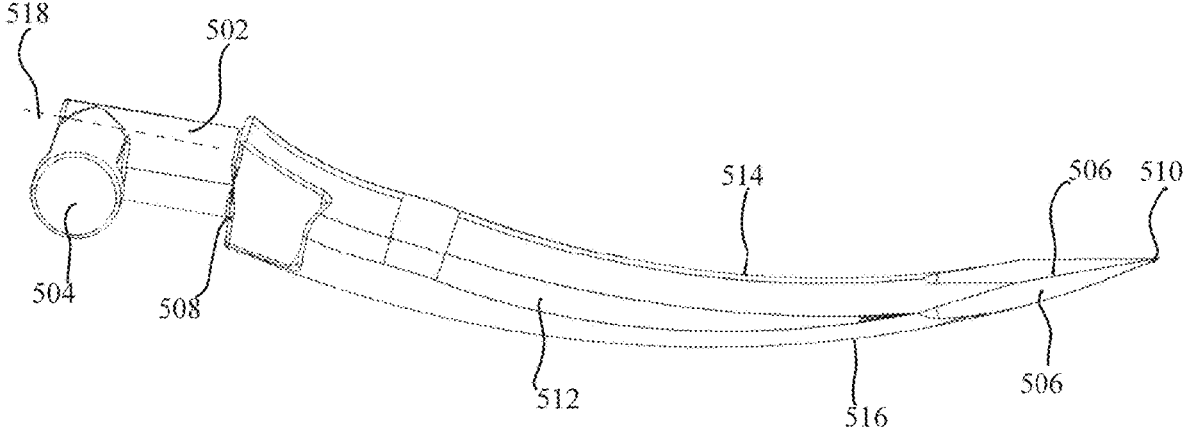
FIG. 17A is a side perspective view of an example bone pin in accordance with the principles of the present disclosure.
Figure 17B:
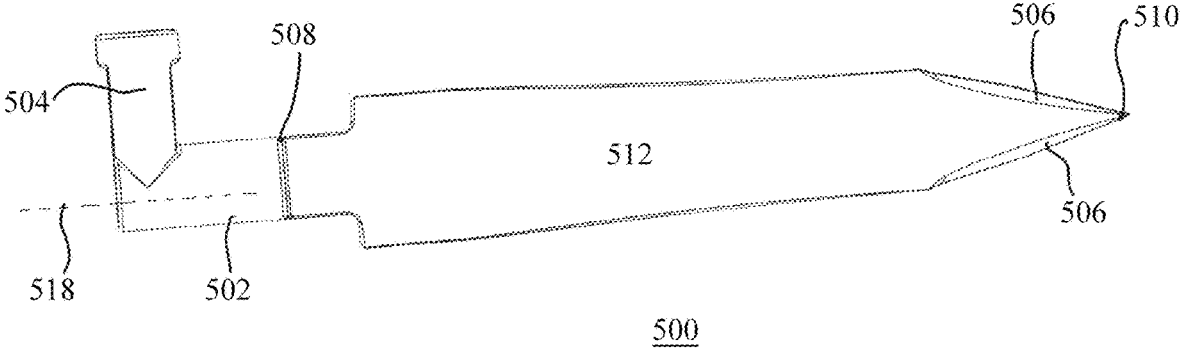
FIG. 17B is a bottom perspective view of an example bone pin in accordance with the principles of the present disclosure.

Referring now to FIGS. 17A and 17B, an embodiment of a bone pin 500 is shown. The bone pin 500 includes a curved body 512. The curved body 512 includes a convex outer surface 516 and a concave inner surface 514. In some embodiments, the surface of the curved body 512 can include two or more faces that meet at an angular juncture and/or two or more faces that meet at a curved juncture resulting in the surface of the body 512 being smooth at some locations and textured at other locations. The curved body 512 extends between a proximal end 508 and a distal end 510 of the bone pin for a pre-determined length. In some embodiments, the body 512 may be curved from end to end and in others the body 512 may be curved from an intermediate point to one end and straight from the intermediate point to the other end. The bone pin 500 also includes a planar surface 506 that converges into distal end 510 at a point. The distal end 510 and/or planar surface 506 may be sufficiently sharp and hard to cut through a substrate so that the bone pin 500 may be driven or impacted into a substrate, such as bone. One or more protrusions (not shown) e.g., barbs, teeth, hooks, spikes, etc. may be disposed along the curved body 512 at various locations and may prevent and/or otherwise facilitate the bone pin 500 from backing out of a substrate. In addition to the protrusions, the curved nature of the body 512 may facilitate anchoring of the bone pin 500 in a substrate e.g., a bony substrate such as a portion of vertebrae. In this way, the curved bone pin 500 may be less prone to back out of a substrate than a similar pin without a curved body 512 and therefore promote better fixation of a spinal implant in a patient's disc space.

Proximal end 508 of bone pin 500 includes a stem 502. In the example embodiment, an arm 504 extends outwardly from the stem 502. The arm 504 may be oriented substantially perpendicular to the stem 502 as shown in FIGS. 17A and 17B. Alternatively, the arm 504 may be oriented at an angle relative to stem 502 and/or arm 504 and it may be hingedly connected. FIGS. 17A and 17B show a medial axis 518 of the stem 502 that runs through the center of the stem 502 and in the lengthwise direction.

Figure 19:
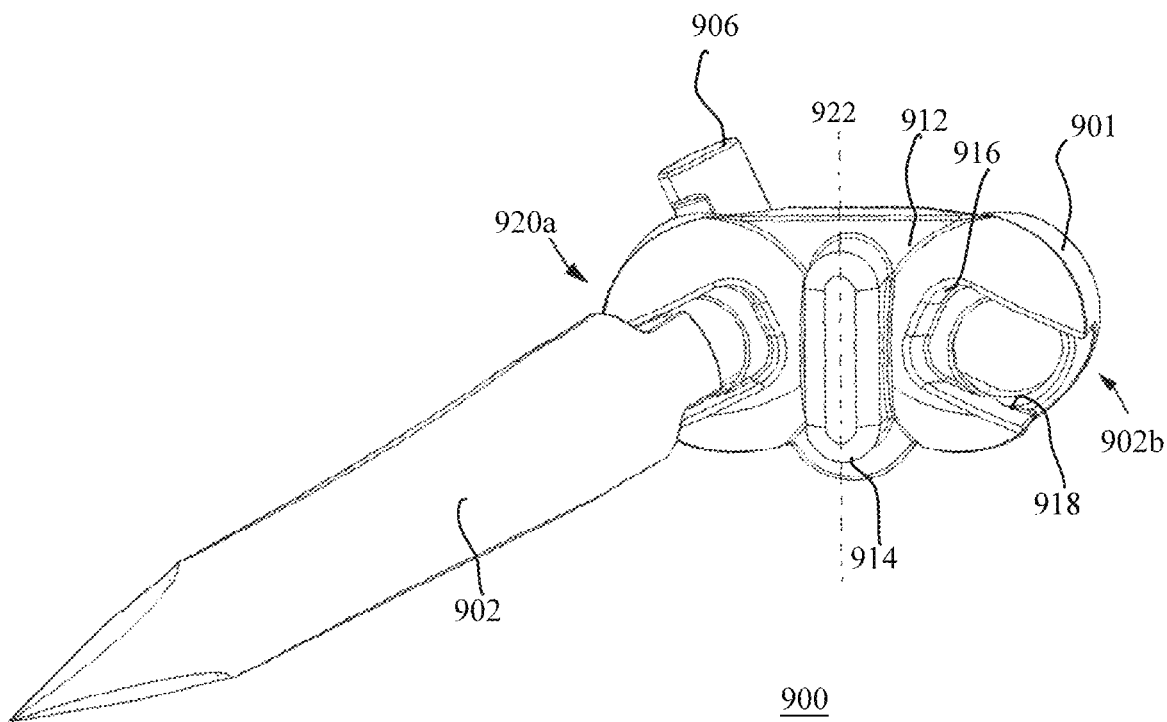
FIG. 19 is an alternative perspective view of an embodiment of a bone pin connector plate in accordance with the principles of the present disclosure.

Referring now to FIGS. 18 and 19, an embodiment of a bone pin anchoring system 900 is shown. In the example illustration, one bone pin is not illustrated for case of understanding. The bone pin anchoring system 900 includes a bone pin connector plate 901 including one or more pin seats 908 that are configured to receive a corresponding bone pin 902. In the illustrated embodiment, the bone pin connector plate 901 includes two pin seats 908 where each pin seat 908 is configured to support a corresponding one bone pin 902. One of the pin seats 908 is located on a first side 920a of the bone pin connector plate 901 and another pin seat 908 is located on a second side 920b of the bone pin connector plate 901. The bone pin seats 908 can be arranged symmetrically about a central axis 922 of the bone pin connector plate 901 or they may be asymmetrical.

A bone pin 902 is inserted into one of the pin seat 908 so that a stem 904 of the bone pin 902 extends through a superior surface 910 and an inferior surface 912 of the bone pin connector plate 900 and the arm 906 extends outside the plane defined by the superior surface 910. The superior surface 910 may at least partially support the arm 906 as shown in FIG. 18. The stem 904 may have a cylindrical body having a circumference or an ovoid body that facilitates rotation of the stem 904 during an installation procedure. The pin seat 908 may include a first interior surface 918 having a circumference slightly larger than the circumference of the cylindrical body of stem 904 and be configured to receive the stem 904. The pin seats 908 may also include a second interior surface 916 having a perimeter that is sufficiently sized to receive the stem 904.

The connector plate 901 also includes a bottom protrusion 914 on the inferior surface 912 that aligns with a corresponding seat on an endplate of a spinal implant so that the connector plate 914 can be aligned in the endplate. The connector plate 901 can reduce excess movement of the bone pins during impaction and while deployed in vertebral bodies. By connecting multiple bone pins the connector plate 901 facilitates stability of the bone pins during impaction during a surgical procedure and reduces the likelihood of the bone pins backing out of vertebral bodies. In various embodiments the bone pins may be pre-loaded to the connector plate 901 to facilitate installation thereof. For example, a surgeon may take a pre-assembled bone pin anchoring system 900 and quickly couple it to a surgical tool for impaction of the bone pins as will be explained in further detail below. The connection of the bone pins by connector plate 901 also allows for simultaneous impaction of multiple bone pins reducing the time required for installation of the pins and the time required for a related surgical procedure.

In some embodiments, various components of the bone pin installation system may be coated or treated with a variety of additives or coatings to improve biocompatibility, bone growth promotion materials such as BMP or other features. For example, bone pin 902 may be selectively coated with bone growth promoting or bone on growth promoting surface treatments that may include, but are not limited to: titanium coatings (solid, porous or textured), hydroxyapatite coatings, or titanium plates (solid, porous or textured), and/or may have various nano-coated or nano-sized features for enhanced bone ingrowth surfaces.

Figure 20:
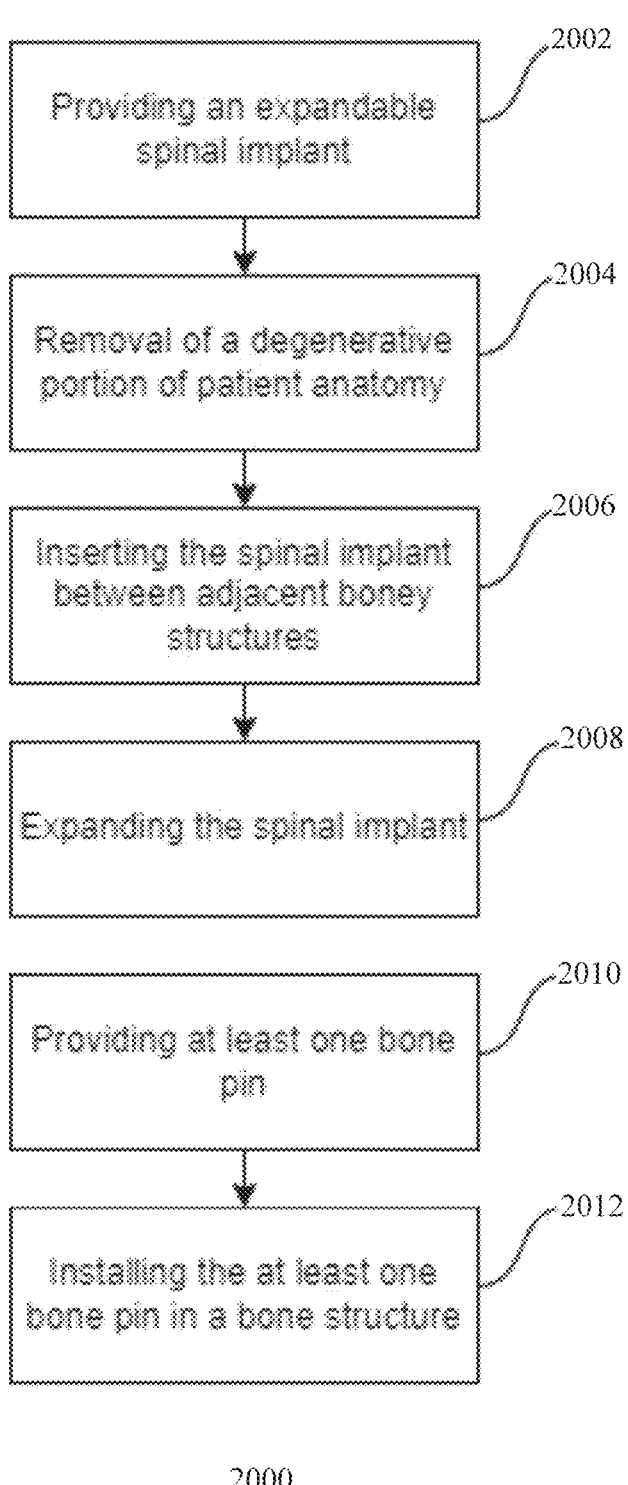
FIG. 20 is a flow chart of a method of operation of various systems and surgical tools in accordance with the principles of the present disclosure.

FIG. 20 is a flow chart method of operation and/or a surgical procedure 2000 for installing an expandable spinal implant and bone pins in and around the vertebrae of a patient. The various method steps below may be explained in the context of the various disclosed spinal implants, e.g., like those shown in FIGS. 1-3. Although the various spinal implants and bone pins disclosed herein may be used to perform the method of operation 2000 the method of operation is not limited to the embodiments disclosed herein. Furthermore, the following steps need not be performed in sequence and can be performed in any alternate sequence with or without all of the disclosed method steps.

At step 2002, an expandable spinal implant may be provided for use in a surgical procedure including, without limitation, corpectomy, discectomy, fusion and/or fixation treatments that employ spinal implants, anterior lumbar interbody fusions (ALIF), posterior lumbar interbody fusion (PLIF), oblique lumbar interbody fusion, transforaminal lumbar interbody fusion (TLIF), various types of anterior fusion procedures, and any fusion procedure in any portion of the spinal column (sacral, lumbar, thoracic, and cervical, for example), open surgery, mini-open surgery, minimally invasive surgery and percutaneous surgical implantation. For example, a surgeon or their staff may prepare the spinal implant for use in a surgical procedure by making it available for use in an operating room, removing the spinal implant from its manufacturing and/or shipping packaging, inspecting the spinal implant or placing the spinal implant on a tray or adjacent to a patient's body. In accordance with various embodiments described herein, the spinal implant may include an endplate, including but not limited to, a lateral endplate, anterior endplate and/or be configured to be connected to one or more surgical tools.

At step 2004, an end user may prepare a space between adjacent boney structures by removal and/or cleaning of the disc space. For example, an end user may remove a degenerative disc between a superior vertebrae and an inferior vertebrae.

At step 2006, an end user may insert the spinal implant in the interbody space between the disc space between the superior vertebrae and the inferior vertebrae. The end user may use a first surgical tool to insert the spinal implant. For example, the user may align the first surgical tool with the lateral endplate of the spinal implant and insert the implant.

At step 2008 an end user may expand the spinal implant to adjust the spacing and angle of inclination of the adjacent vertebrae. For example, the end user may use the first surgical tool to expand and/or angulate the spinal implant. The user may then use the first surgical tool to adjust the positioning of the spinal implant in the interbody space and the angulation of one or more endplates of the spinal implant.

At step 2010 one or more bone pins may be provided. For example, a surgeon or their staff may prepare the one or more bone pins for use in a surgical procedure by making the one or more bone pins available for use in the operating room, removing the bone pins from their manufacturing and/or shipping packaging, inspecting the bone pins or placing the bone pins on a tray or adjacent to a patient's body. The one or more bone pin may be part of an anchoring system, in accordance with various embodiments described herein, which may be prepared for use in a surgical procedure in a similar manner to the bone pins described above. For example, one or more anchoring systems having a connector plate with one or more bone pins received with the connector plate may be provided. One or more connector plate apertures of a guide can be loaded with the one or more anchoring systems. In some embodiments, the guide is loaded with an anchoring system in each anchor aperture. The guide may be pre-loaded, that is loaded in advance of this method 2000 and/or step 2010, with one or more anchoring systems and/or bone pins. For example, the anchoring system and bone pins may be preassembled such that the bone pins are attached to the anchoring system as a single unit that allows far rapid installation of the bone pins. Alternatively, an end user may insert, manually or by any other means, the one or more anchoring systems and/or bone pins into the guide at this step 2010. The bone pins and/or anchoring systems may, for example, be used in any surgical procedures or techniques discussed herein.

At step 2012, an end user e.g., a surgeon, may deploy or impact the one or more bone pins into a bony structure. The user may insert a guide rod on the end of the guide into a central alignment aperture of an end plate of the spinal implant previously inserted between vertebral bodies in step 2006. The insertion of the rod in the central alignment aperture aligns the guide, anchoring systems and bone pins properly with the implant e.g., in an orientation so that the bone pins may be impacted into the area surrounding the implant so that the pins are correctly positioned relative to one or more bone pin apertures, or other component of the implant.

Following alignment of the guide with the implant, the user may release a stop on the guide that is configured to control the depth at which the user may insert the guide into the interbody space. As described herein, the stop may be aligned with a nearby vertebral body or other bony structure while the guide is aligned with the implant. For example, the stop may be initially non-deployed and if desired by the surgeon the stop may be deployed to prevent over insertion of the surgical tool.

The user can optionally attach a wedge to a pushing element of the second surgical tool to control the impaction depth of the pushing element. The wedge can be configured to control the depth at which the pushing element impacts the bone pin anchoring systems and/or bone pins. The user may apply a force with a hammer or similar tool to a flat head or other portion of the pushing element so that the pushing element exerts an impaction force on the one or more bone pins of the anchoring system sufficient to drive the one or more bone pins into bony anatomy. In some embodiments, the pushing element may be used to partially impact the bone pin anchoring systems up to the maximum depth allowed by the wedge. Note that different sized wedges may be available so the user can select the impaction depth allowed by the wedge. After partial impaction the one or more bone pins may be partially lodged in a vertebral body and partially lodged in the one or more anchor apertures of the guide thereby restricting removal of the second surgical tool at this step.

Following partial impaction the user can complete final impaction of the bone pins and/or anchoring systems by removing the wedge and using a hammer directly driving the bone pins and/or anchoring systems or other impaction device. Another example impaction device may comprise a rotatable driver having a threaded connection that moves a fork forward to perform a final impaction as described herein. This type of tool will allow a surgeon to continue to impact the anchoring systems so that the pins penetrate the vertebral bodies at the desired depth i.e., the depth needed to secure the implant in accordance with the relevant surgical procedure. The user may then remove the second surgical tool from the interbody space leaving the anchoring system in place. If there are one or more pin locks, cams, plates or other fastening mechanisms they may be secured to cover the bone pins following completing the impaction of the bone pins to prevent the bone pins and/or anchoring systems from backing out. For example, the user may move bone screw lock 803 in FIG. 1 from the unlocked position to the locked position to cover, or at least partially cover, the bone pins and/or anchoring systems.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

Without excluding further possible embodiments, certain example embodiments are summarized in the following clauses:

Clause 1: An anchoring system for use in a surgical procedure, comprising: one or more bone pins having a curved body extending from a proximal end to a distal end, and the proximal end comprising a support arm; and a connector plate having a superior surface, an inferior surface, and one or more pin seats extending between the superior surface and the inferior surface, wherein each of the one or more pin seats are configured to receive a corresponding one of the one or more bone pins such that the support arm of the corresponding one or more bone pins is pivotally supported, and wherein the curved body of the one or more bone pins is configured to facilitate anchoring of the one or more bone pins in bony anatomy.

Clause 2: The anchoring system of clause 1, wherein the distal end of each of the one or more bone pins further comprises a planar portion terminating at a point for cutting through bony anatomy.

Clause 3: The anchoring system of any one of clauses 1-2, wherein each of the one or more bone pins further comprises one or more protrusions arranged on the curved body and configured to facilitate anchoring of the bone pin in bony anatomy.

Clause 4: The anchoring system of clause 3, wherein the connector plate further comprises at least one bulbous protrusion having a size and shape that corresponds to a size and shape of an aperture of an endplate of a spinal implant thereby facilitating stability and alignment of the anchoring system relative to the spinal implant.

Clause 5: The anchoring system of clause 4, wherein the endplate further comprises at least one rotatable bone pin lock having at least one wing, each wing comprising a surface extending in a plane that is substantially perpendicular to a corresponding bone pin trajectory and the at least one rotatable bone pin lock is configured to secure a bone pin in the endplate.

Clause 6: The anchoring system of any one of clauses 1-5, wherein each of the one or more bone pins include a hydroxyapatite coating and each of the one or more bone pins is pre-loaded to the anchoring system such that each of the one or more bone pins may be driven into patient anatomy.

Clause 7: The anchoring system of clause 4, wherein the at least one bulbous protrusion is configured to align the connector plate relative to the spinal implant without directly coupling the connector plate to the spinal implant.

Clause 8: The anchoring system of any one of clauses 1-7, wherein each of the one or more bone pins further comprises a stem and wherein, during an installation procedure, the one or more bone pins are configured to rotate relative to a medial axis of the stem and to diverge in a controlled manner from a central axis of the connector plate as the pins rotate.

Clause 9: The anchoring system of clause 8, wherein the one or more bone pins comprises a first bone pin and a second bone pin and wherein, during an installation procedure, the first bone pin is configured to rotate in a first direction while the second bone pin rotates in a second direction, the second direction being different than the first direction.

Clause 10: A bone pin installation system, the system comprising: a hollow surgical tool extending in a longitudinal direction and having a guide portion at a distal end thereof; one or more bone pins having a curved body extending from a proximal end to a distal end and a support arm; and one or more connector plates having a superior surface, an inferior surface and one or more pin seats extending between the superior surface and the inferior surface, wherein the one or more pin seats are configured to receive a corresponding one of the one or more bone pins so that the support arm of the corresponding bone pin is pivotally supported by the superior surface, wherein the guide portion includes one or more channels configured to receive the support arm of a corresponding one of the one or more bone pins and guide the corresponding bone pin during an installation procedure, wherein the curved body of the one or more bone pins is configured to facilitate anchoring of the one or more bone pins in bony anatomy.

Clause 11: The bone pin installation system of clause 10, the one or more bone pins further comprising a stem and being received in a corresponding one of the one or more connector plates, wherein the one or more bone pins are configured to rotate in the one or more channels relative to a medial axis of the stem and the distal end of the one or more bone pins diverges in a controlled manner from a central axis of the corresponding one of the one or more connector plates as the one or more bone pins rotate.

Clause 12: The bone pin installation system of clauses 10-11, wherein a distal end of the guide portion further comprises a guide rod, configured to align with a central aperture of a spinal implant.

Clause 13: The bone pin installation system of clauses 10-12, wherein the hollow surgical tool further comprises a depth stop configured to contact a bony structure of a patient, wherein the depth stop is configured to limit the depth of insertion of the surgical tool into an interbody space.

Clause 14: The bone pin installation system of clauses 10-13, wherein the guide portion further comprises one or more anchor apertures configured to receive the one or more connector plates.

Clause 15: The bone pin installation system of clause 14, wherein the guide portion further comprises a deflection tab proximate to each of the anchor apertures, wherein the deflector tab extends outward relative to the longitudinal direction of the surgical tool so as to allow the connector plate to be positioned within a groove on a surface of the guide portion and temporarily coupled in place relative to the groove.

Clause 16: The bone pin installation system of clause 14, further comprising a pusher insertable inside of the surgical tool, wherein the pusher is configured to drive the one or more connector plates by applying an impaction force to the one or more connector plates.

Clause 17: The bone pin installation system of clause 16, wherein the pusher further comprises one or more prongs at a distal end thereof configured to be received in the one or more anchor apertures.

Clause 18: The bone pin installation system of clause 17, further comprising a wedge separably attached to a proximal end of the pusher, wherein the wedge is configured to control the depth at which the one or more prongs are received in the one or more anchor apertures thereby controlling an impaction depth of the one or more bone pins.

Clause 19: A method of inserting an expandable spinal implant comprising: preparing a spinal implant for insertion in a patient; removing a degenerative portion of patient anatomy; inserting the spinal implant between one or more bony structures of a patient; preparing one or more anchoring systems according to claim 1 for insertion into the patient, wherein each of the one or more bone pins is pre-loaded into one or more anchor apertures of a guide portion; an aligning step including aligning a guide rod of the guide portion with a central aperture of an endplate of the spinal implant; an impacting step including impacting the one or more anchoring systems into bony anatomy using a pusher; and locking one or more fastening mechanisms of the spinal implant.

Clause 20: The method of clauses 19, wherein, during the impacting step, each of the one or more bone pins diverges away from a medial axis of the connector plate.

What is claimed is:

1. An anchoring system for use in a surgical procedure, comprising:
   one or more bone pins each having a curved body extending from a proximal end to a distal end, and the proximal end comprising a stem; and
   a connector plate having a superior surface, an inferior surface, and one or more pin seats extending between the superior surface and the inferior surface,
   wherein each of the one or more pin seats are configured to receive a corresponding one of the one or more bone pins such that the one or more bone pins are configured to rotate within the one or more pin seats about a medial axis of the stem causing the respective distal ends of each of the one or more bone pins to diverge from a central axis of the connector plate, and
   wherein the curved body of the one or more bone pins is configured to facilitate anchoring of the one or more bone pins in bony anatomy.

2. The anchoring system of claim 1, wherein the distal end of each of the one or more bone pins further comprises a planar portion terminating at a point for cutting through bony anatomy.

3. The anchoring system of claim 1, wherein each of the one or more bone pins further comprises one or more protrusions arranged on the curved body and configured to facilitate anchoring of the one or more bone pins in bony anatomy.

4. The anchoring system of claim 3, wherein the connector plate further comprises at least one bulbous protrusion having a size and shape that corresponds to a size and shape of an aperture of an endplate of a spinal implant thereby facilitating stability and alignment of the anchoring system relative to the spinal implant.

5. The anchoring system of claim 4, wherein the endplate further comprises at least one rotatable bone pin lock having at least one wing, each wing comprising a surface extending in a plane that is substantially perpendicular to a corresponding bone pin trajectory and the at least one rotatable bone pin lock is configured to secure a bone pin in the endplate.

6. The anchoring system of claim 4, wherein the at least one bulbous protrusion is configured to align the connector plate relative to the spinal implant without directly coupling the connector plate to the spinal implant.

7. The anchoring system of claim 1, wherein each of the one or more bone pins includes a hydroxyapatite coating and each of the one or more bone pins is pre-loaded to the anchoring system such that each of the one or more bone pins may be driven into patient anatomy.

8. The anchoring system of claim 1, wherein the one or more bone pins comprises a first bone pin and a second bone pin and wherein, during an installation procedure, the first bone pin is configured to rotate in a first direction while the second bone pin rotates in a second direction, the second direction being different than the first direction.

9. The anchoring system of claim 8, the connector plate further comprising a first channel corresponding to the first bone pin and a second channel corresponding to the second bone pin, wherein the first channel follows a first trajectory configured to cause the first bone pin to rotate in the first direction and diverge from the central axis of the connector plate and the second channel follows a second trajectory configured to cause the second bone pin to rotate in the second direction and diverge from the central axis of the connector plate.

10. A bone pin installation system, the system comprising:
a hollow surgical tool extending in a longitudinal direction and having a guide portion at a distal end thereof;
one or more bone pins each having a curved body extending from a proximal end to a distal end and a stem; and
one or more connector plates having a superior surface, an inferior surface and one or more pin seats extending between the superior surface and the inferior surface,
wherein the one or more pin seats are configured to receive a corresponding one of the one or more bone pins so that the one or more bone pins are configured to rotate within the one or more pin seats about a medial axis of the stem causing the respective distal ends of each of the one or more bone pins to diverge from a central axis of the connector plate,
wherein the guide portion includes one or more channels configured to receive the one or more bone pins and guide the bone pins during an installation procedure,
wherein the curved body of the one or more bone pins is configured to facilitate anchoring of the one or more bone pins in bony anatomy.

11. The bone pin installation system of claim 10, wherein the one of more bone pins are received in a corresponding channel of the one or more connector plates, wherein the one or more bone pins are configured to rotate in the corresponding channels about a medial axis of the stem and each of the distal ends of the one or more bone pins diverges in a controlled manner from a central axis of the corresponding one of the one or more connector plates as the one or more bone pins rotate.

12. The bone pin installation system of claim 10, wherein a distal end of the guide portion further comprises a guide rod, configured to align with a central aperture of a spinal implant.

13. The bone pin installation system of claim 10, wherein the hollow surgical tool further comprises a depth stop configured to contact a bony structure of a patient, wherein the depth stop is configured to limit the depth of insertion of the surgical tool into an interbody space.

14. The bone pin installation system of claim 10, wherein the guide portion further comprises one or more anchor apertures configured to receive the one or more connector plates.

15. The bone pin installation system of claim 14, wherein the guide portion further comprises a deflection tab proximate to each of the anchor apertures, wherein the deflection tab extends outward relative to the longitudinal direction of the surgical tool so as to allow the connector plate to be positioned within a groove on a surface of the guide portion and temporarily coupled in place relative to the groove.

16. The bone pin installation system of claim 14, further comprising a pusher insertable inside of the surgical tool, wherein the pusher is configured to drive the one or more connector plates by applying an impaction force to the one or more connector plates.

17. The bone pin installation system of claim 16, wherein the pusher further comprises one or more prongs at a distal end thereof configured to be received in the one or more anchor apertures.

18. The bone pin installation system of claim 17, further comprising a wedge separably attached to a proximal end of the pusher, wherein the wedge is configured to control the depth at which the one or more prongs are received in the one or more anchor apertures thereby controlling an impaction depth of the one or more bone pins.

19. A method of inserting an expandable spinal implant comprising:
preparing the expandable spinal implant for insertion in a patient;
removing a degenerative portion of patient anatomy;
inserting the expandable spinal implant between one or more bony structures of the patient;
preparing one or more anchoring systems according to claim 1 for insertion into the patient, wherein each of the one or more bone pins is pre-loaded into one or more anchor apertures of a guide portion of a surgical tool;
an aligning step including aligning a guide rod of the guide portion with a central aperture of an endplate of the expandable spinal implant;
an impacting step including impacting the one or more anchoring systems into bony anatomy using a pusher; and
locking one or more fastening mechanisms of the expandable spinal implant.

20. The method of claim 19, wherein, during the impacting step, each of the one or more bone pins diverges away from a medial axis of the connector plate.

* * * * *